(12) United States Patent
Irving

(10) Patent No.: US 7,083,624 B2
(45) Date of Patent: Aug. 1, 2006

(54) EXTRAMEDULLARY FLUOROSCOPIC ALIGNMENT GUIDE

(75) Inventor: John F. Irving, Hamden, CT (US)

(73) Assignee: Depuy Products, Inc., Warsaw, IN (US)

(*) Notice: Subject to any disclaimer, the term of this patent is extended or adjusted under 35 U.S.C. 154(b) by 337 days.

(21) Appl. No.: 10/350,378

(22) Filed: Jan. 23, 2003

(65) Prior Publication Data

US 2004/0015173 A1 Jan. 22, 2004

Related U.S. Application Data

(60) Provisional application No. 60/351,782, filed on Jan. 25, 2002.

(51) Int. Cl.
*A61F 5/00* (2006.01)
(52) U.S. Cl. ...................................................... 606/87
(58) Field of Classification Search ............ 606/86–89, 606/96–98
See application file for complete search history.

(56) References Cited

U.S. PATENT DOCUMENTS

| | | | | |
|---|---|---|---|---|
| 4,938,762 | A * | 7/1990 | Wehrli ........................ | 606/88 |
| 5,021,056 | A * | 6/1991 | Hofmann et al. ............ | 606/86 |
| 5,162,039 | A * | 11/1992 | Dahners ...................... | 602/23 |
| 5,228,459 | A * | 7/1993 | Caspari et al. ............... | 606/88 |
| 5,306,276 | A * | 4/1994 | Johnson et al. .............. | 606/86 |
| 5,628,749 | A * | 5/1997 | Vendrely et al. ............ | 606/80 |
| 5,628,750 | A * | 5/1997 | Whitlock et al. ............ | 606/88 |
| 5,681,320 | A * | 10/1997 | McGuire ..................... | 606/88 |
| 5,716,361 | A | 2/1998 | Masini | |
| 5,908,424 | A * | 6/1999 | Bertin et al. ................. | 606/88 |
| 6,036,696 | A | 3/2000 | Lambrecht et al. | |
| 6,090,114 | A * | 7/2000 | Matsuno et al. ............. | 606/86 |
| 6,214,013 | B1 | 4/2001 | Lambrecht et al. | |
| 6,267,762 | B1 | 7/2001 | Millard | |
| 6,423,061 | B1 | 7/2002 | Bryant | |

OTHER PUBLICATIONS

Teter, K.E. et al.: Accuracy of Intramedullary Versus Extramedullary Tibial Alignment Cutting Systems in Total Knee Arthroplasty. CORR 321: 106-110, 1995.

(Continued)

*Primary Examiner*—Eduardo C. Robert
*Assistant Examiner*—Richard Shaffer

(57) ABSTRACT

An extramedullary fluoroscopic alignment guide is disclosed, along with a surgical kit including such an alignment guide and a surgical method employing such an alignment guide. The extramedullary alignment guide includes both radiolucent and radiopaque material. The invention is useful in performing surgery on bones, for example, in performing surgery on the knee joint. The radiolucent material provides a support structure for the radiopaque material. The radiopaque material provides a radiopaque instrument reference that is sized, shaped and positioned so that the surgeon can simultaneously fluoroscopically view the patient's bone and the radiopaque instrument reference. The radiopaque instrument reference may be aligned with landmarks on the bone or other fluoroscopically viewable bones, such as the mechanical or anatomic axis. The guide may be provided as part of a kit with anchoring members and a cutting guide. The anchoring members can be set using the alignment guide. The alignment guide can then be removed while leaving the anchoring members in place to serve as a benchmark for the cutting guide.

14 Claims, 21 Drawing Sheets

OTHER PUBLICATIONS

Sanders, R. et al.: Exposure of the Orthopaedic Surgeon to Radiation. IBIS 75-A: 326-330, 1993.

Dennis, D.A. et al.: Intramedullary Versus Extramedullary Tibial Alignment Systems in Total Knee Arthroplasty. JOA 8: 43-47, 1993.

Oswald, M.H. et al.: Radiological Analysis of Normal Axial Alignment of Femur and Tibia in View of Total Knee Arthroplasty. JOA 8: 419-426, 1993.

Lonner et al.: Effect of Rotation and Knee Flexion on Radiographic Alignment in Total Knee Arthroplasties. CORR 331: 102-106, 1996.

Perillo-Marcone, A. et al.: The Importance of Tibial Alignment, JOA 15: 1020-1027, 2000.

Cates, H.E. et al.: Intramedullary Versus Extramedullary Femoral Alignment Systems in Total Knee Replacement. CORR 286: 32-39, 1993.

Kennedy, W.RR. et al.: Unicompartmental Arthroplasty of the Knee. CORR 221: 278-285, 1987.

Bert, J.M. et al.: Universal Intramedullary Instrumentation for Unicompartmental Total Knee Arthroplasty. CORR 271: 79-87, 1991.

Evans, P.D., FRCS (Orth) et al.: Radiological Study of the Accuracy of a Tibial Intramedullary Cutting Guide for Knee Arthroplasty. *The Journal of Arthroplasty*, vol. 10 No. 1: pp. 43-46, 1995.

Reed, S.C. et al.: The Accuracy of Femoral Intramedullary Guides in Total Knee Arthroplasty. JOA 12: 677-682, 1997.

Thornhill, T.S. in Goldberg, V.M. Controversies of Total Knee Arthroplasty: Unicompartmental Total Knee Arthroplasty, 7-18, Raven Press, 1991.

Krackow, K.A. and Hungerford, D.S. in Goldbery, V.M. Controversies of Total Knee Arthroplasty; Sequence of Reconstruction and Alignment in Total Knee Arthroplasty, Churchhill Livingstone, 1991, pp. 193-208.

Rosenberg, A. G., in Rand, J.A. *Total Knee Arthroplasty*; Surgical Technique of Posterior Cruciate Sacrificing, and Preserving Total Knee Arthroplasty, 115-153, Raven Press, 1993.

Marmor, L. in Rand, J.A. *Total Knee Arthroplasty*; Unicompartmental Knee Replacement, 245-280, Raven Press, 1993.

Scott, R.D. *Techniques in Orthopaedisc Journal*; Robert Brigham Unicondylar Knee surgical technique, 15-23, Aspen Publication, Apr. 1990.

Rand, J.A. Revision Total Knee Arthroplasty: Techniques and Results, in Morrey, B.F.: *Joint Replacement Arthroplasty* New York, NY, Churchill Livingstone, 1991, pp. 1093-1111.

Symposia III: Unicompartmental TKR in the Millennium in the Knee Society/ AAHKS Combined Specialty Day Meeting, AAOS, San Francisco, CA Mar. 2001.

Greene Tweed Medical and Biotechnology, The ORTHTEK™ Targeting Guide, http://www.gtweed.com/Medical&Biotech/SurgicalInstruments.htm, 2001.

* cited by examiner

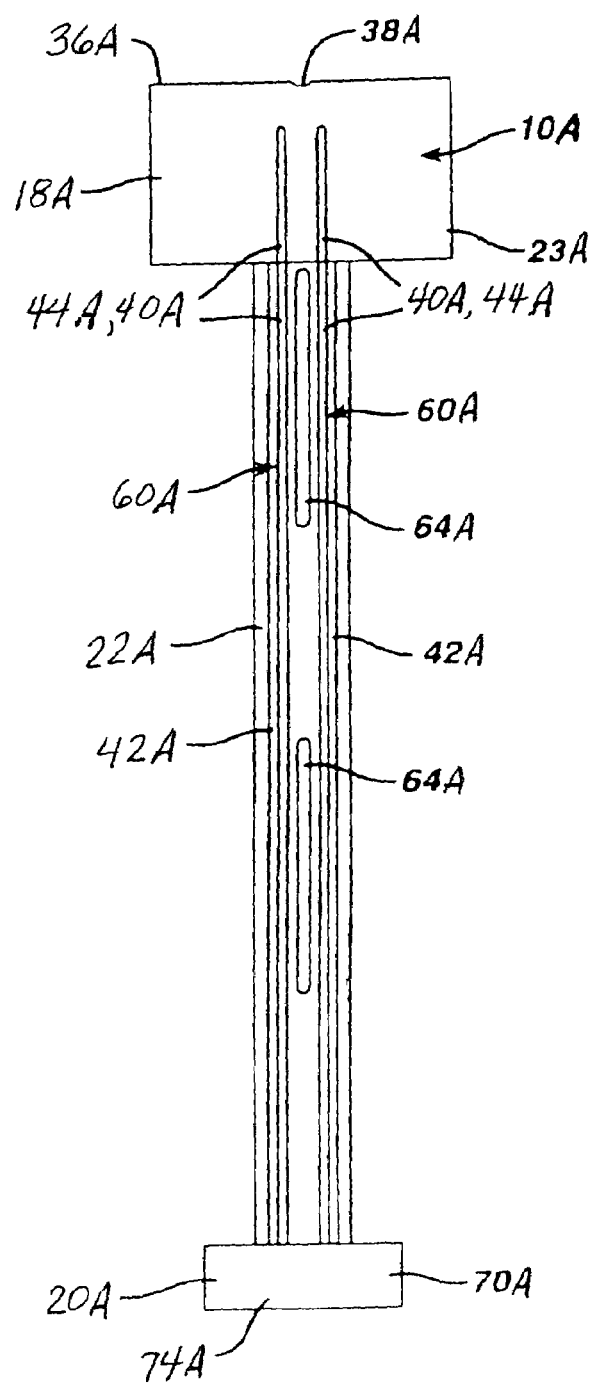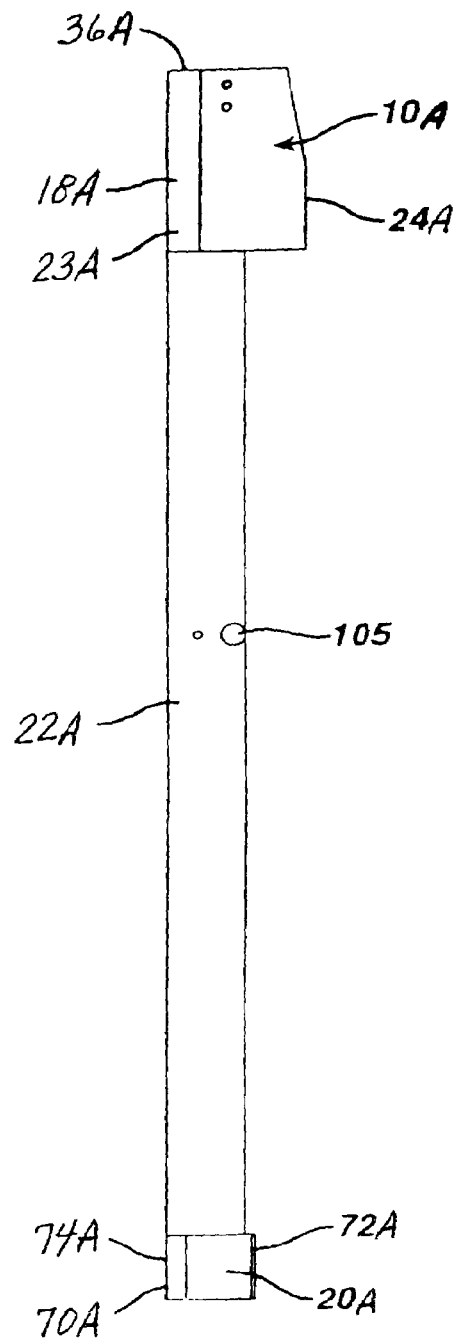

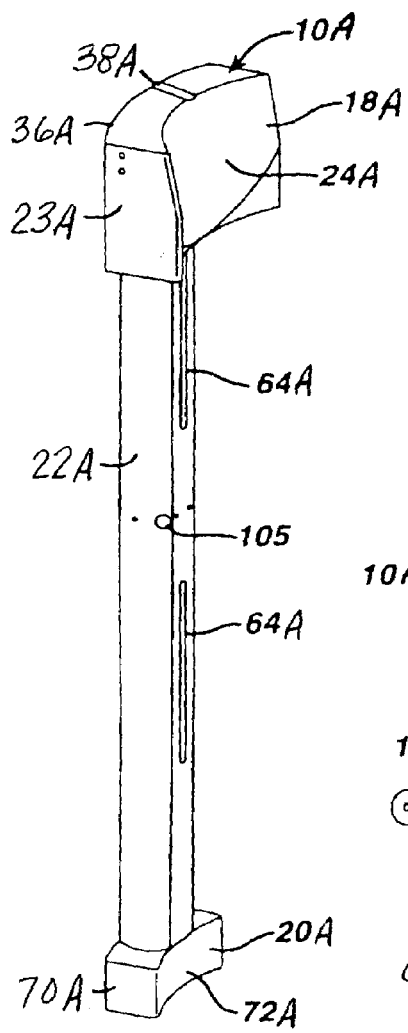
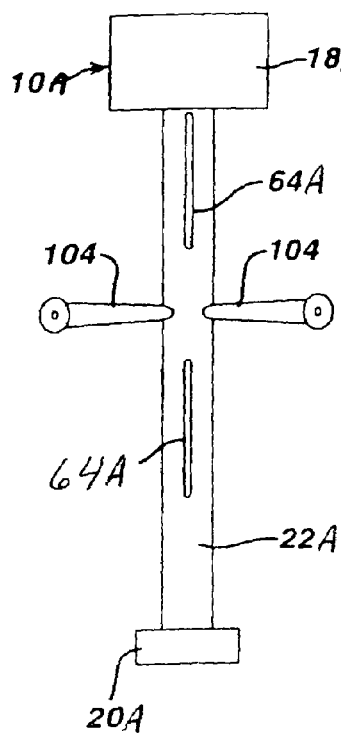
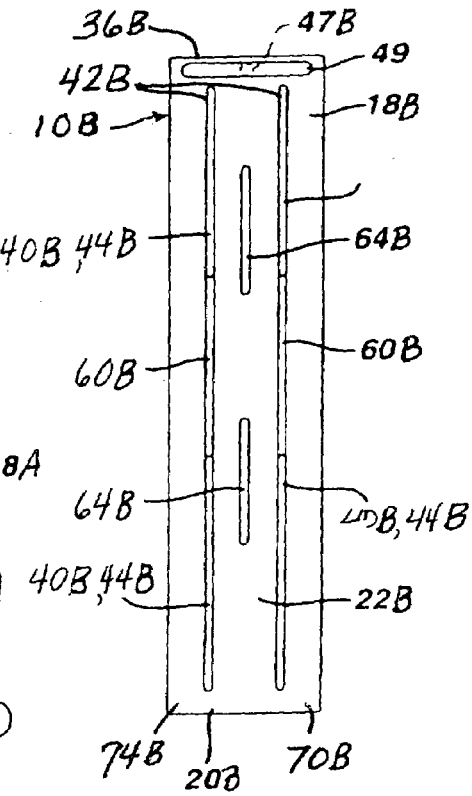

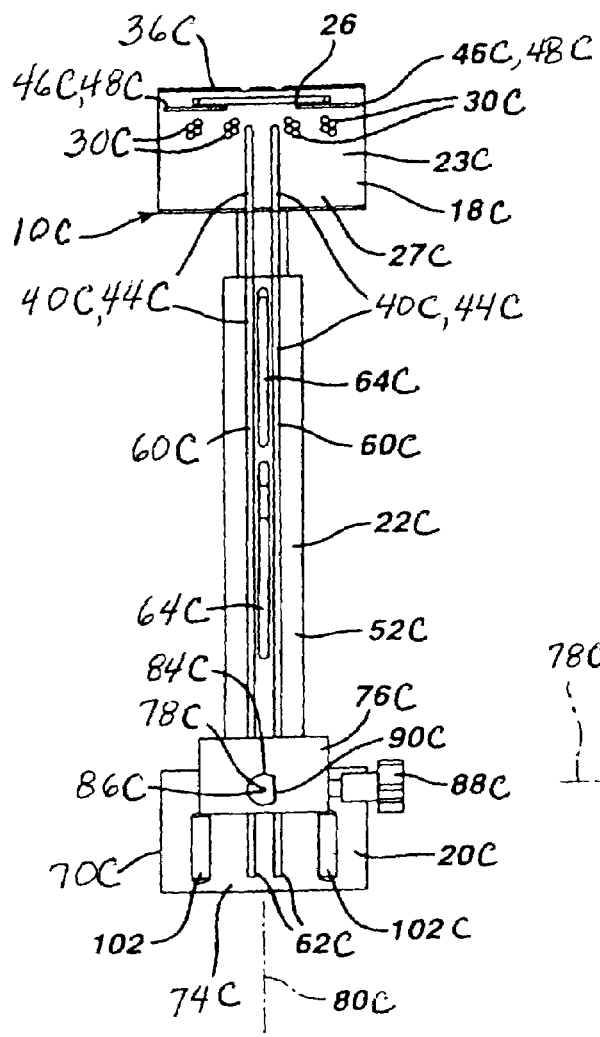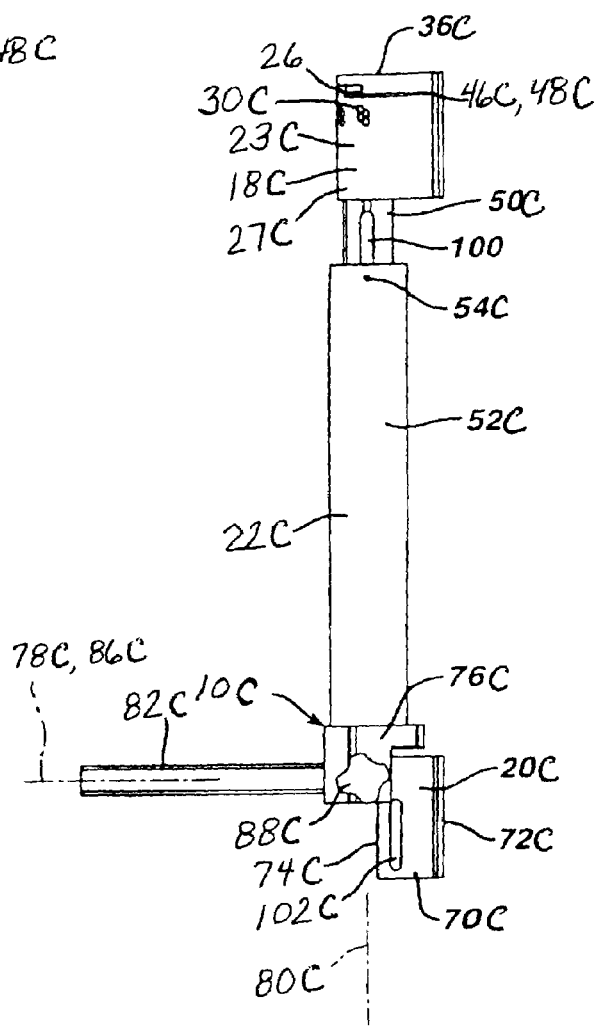

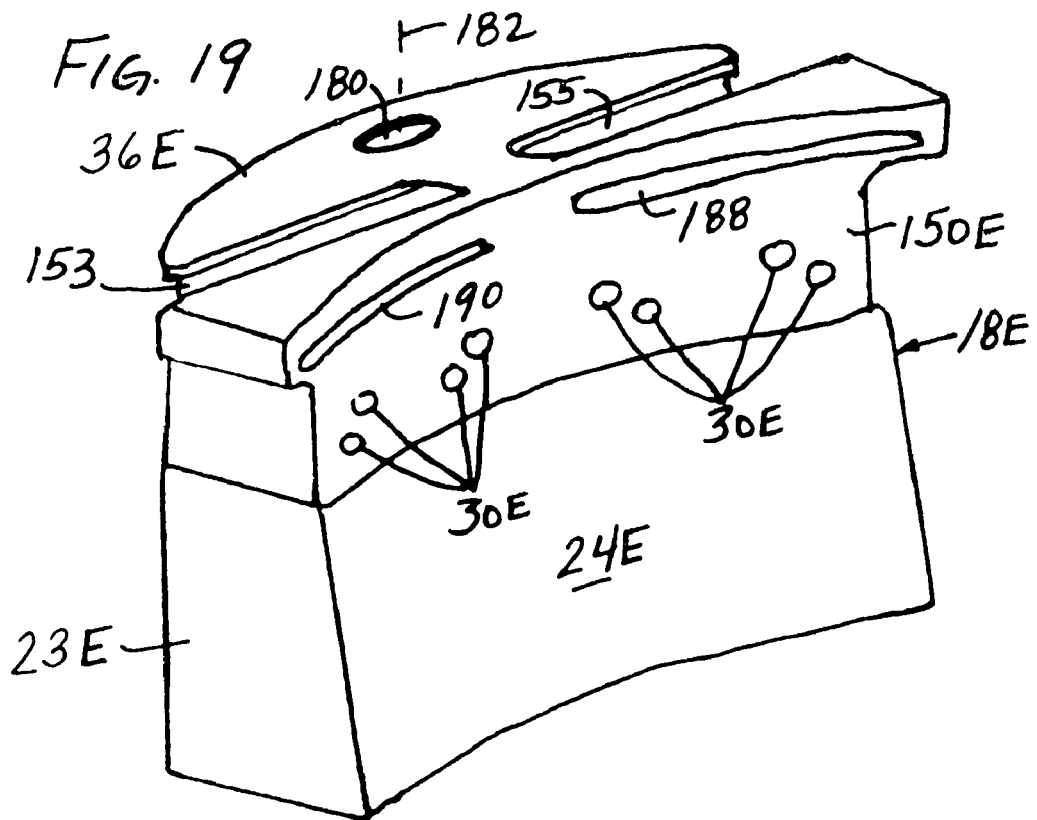
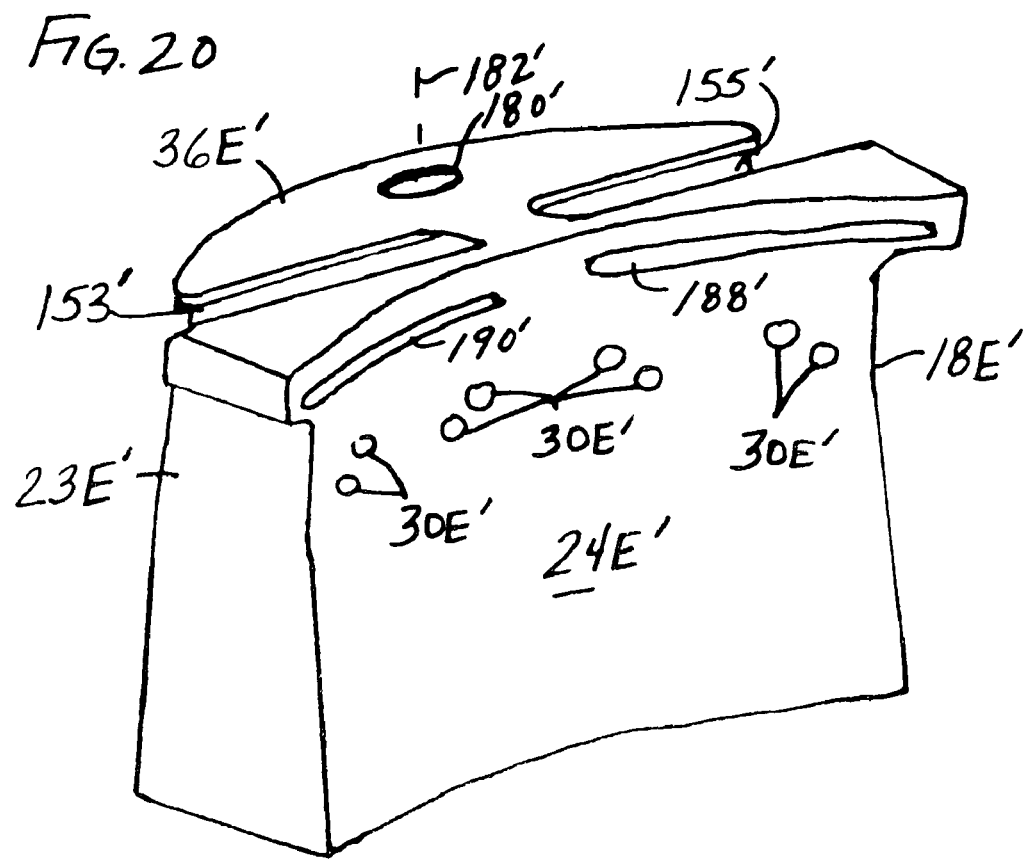

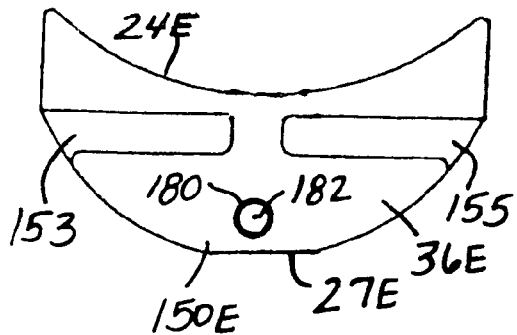
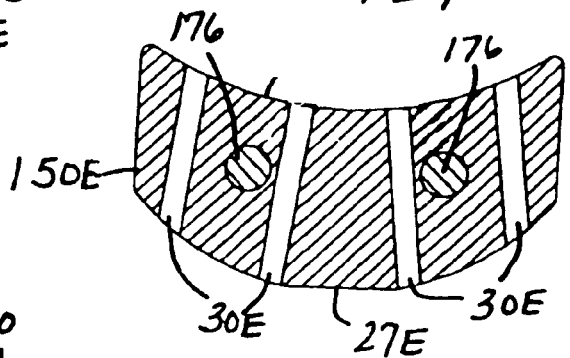
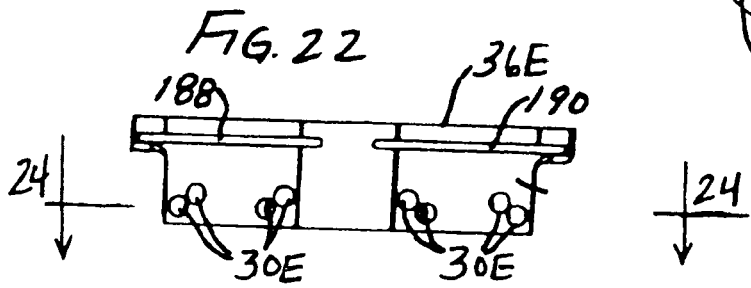
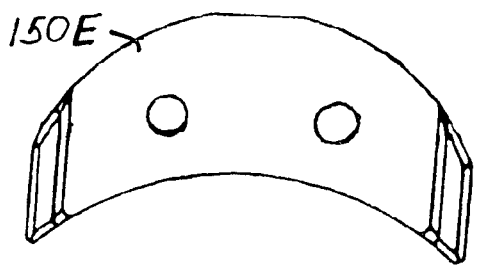

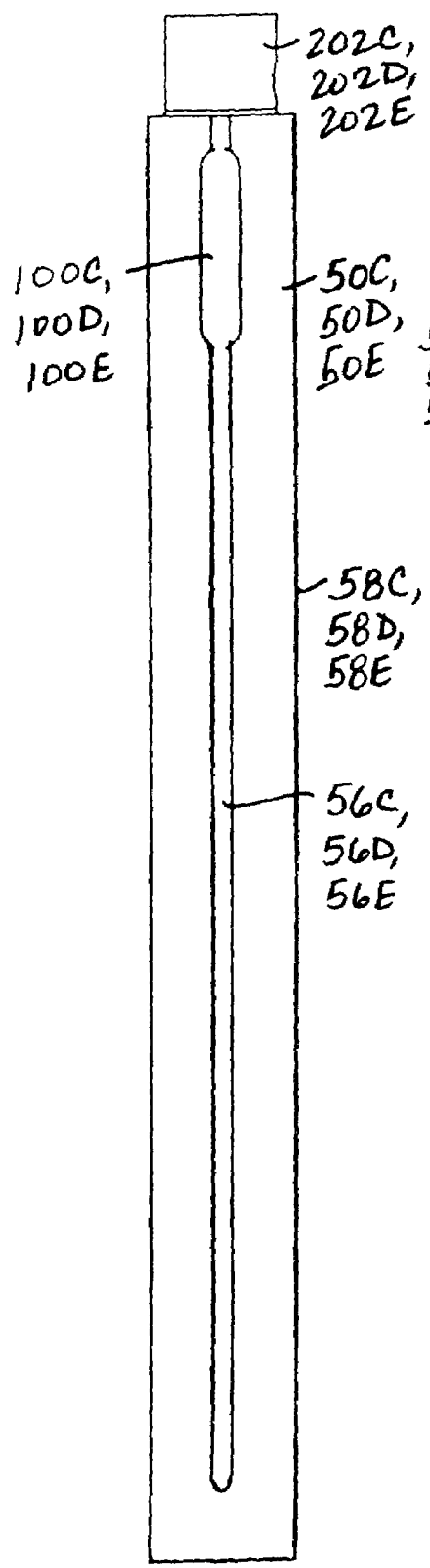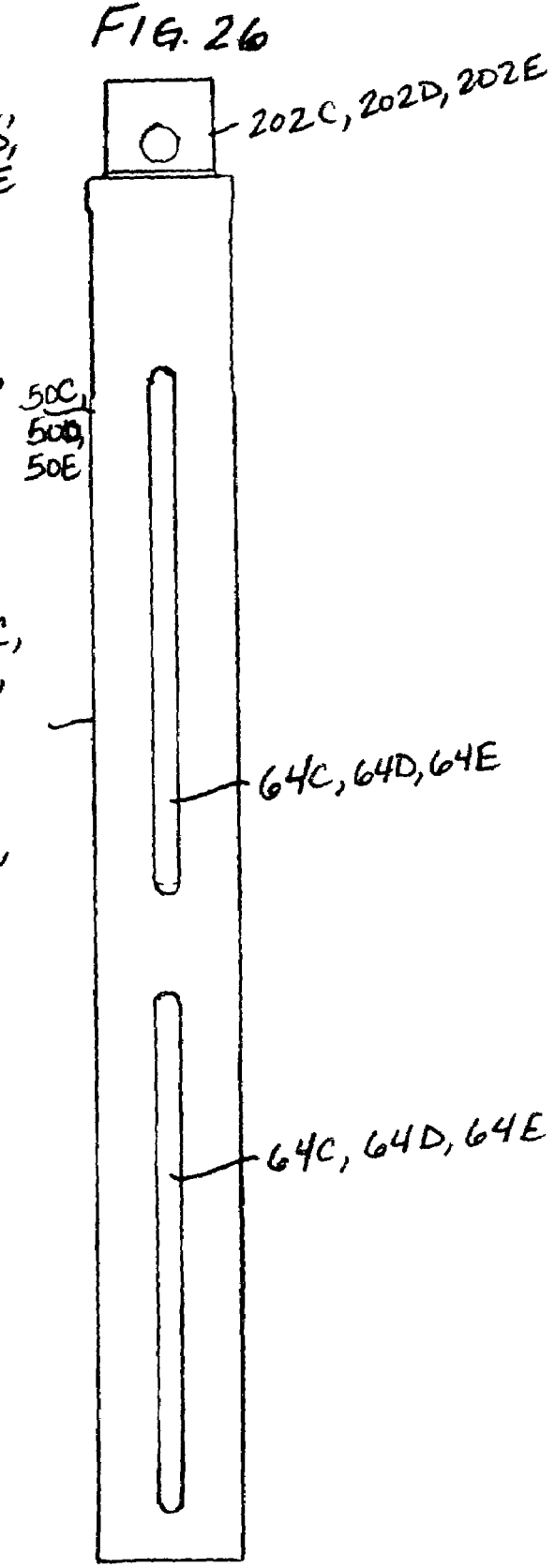

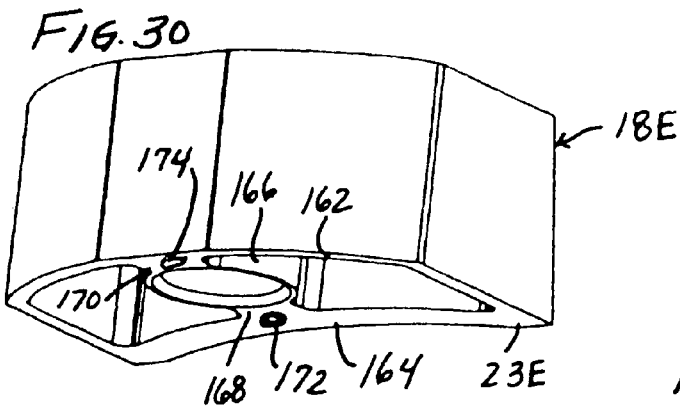
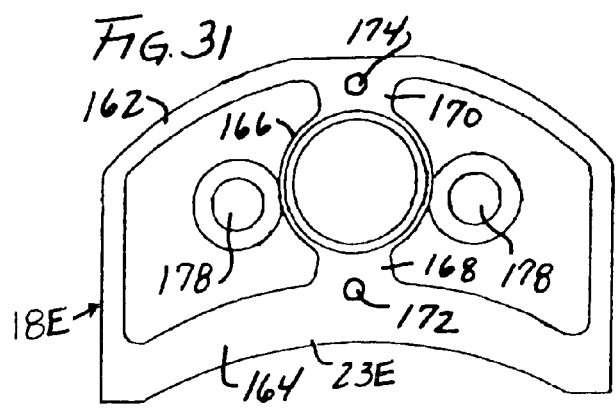
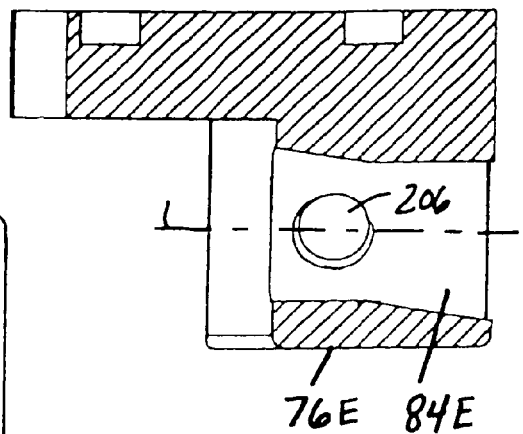
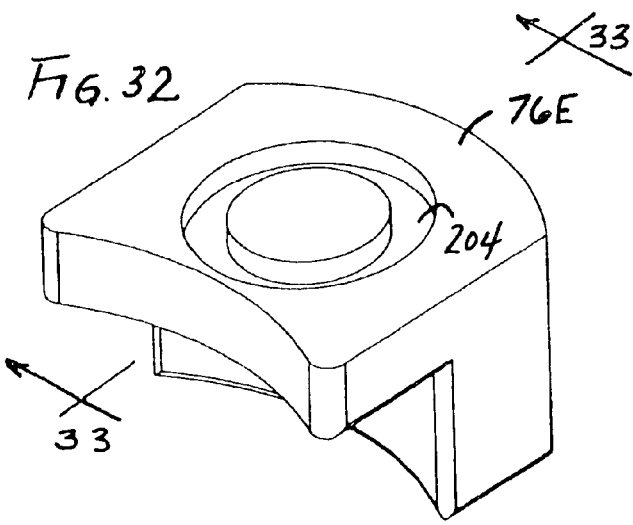

EXTRAMEDULLARY FLUOROSCOPIC ALIGNMENT GUIDE

CROSS REFERENCE TO U.S. PROVISIONAL PATENT APPLICATION

This application is a Utility Application based upon U.S. Provisional Patent Application Ser. No. 60/351,782, filed Jan. 25, 2002, and entitled EXTRAMEDULLARY FLUOROSCOPIC ALIGNMENT GUIDE, the complete disclosure of which is incorporated by reference herein.

BACKGROUND OF THE INVENTION

1. Field of the Invention

The present invention relates to an extramedullary fluoroscopic alignment guide for use in joint replacement surgery. The fluoroscopic alignment guide of the present invention may be particularly useful in less-invasive surgical procedures, such as in unicompartmental knee replacement. The present invention also relates to a surgical method for resection of a bone, and may be particularly useful in resecting a tibia for knee arthroplasty.

2. Description of the Prior Art

The surgical preparation of bone endings for receiving prosthetic joints for either a total or partial joint replacement is a complex procedure. A number of bone cuts are made to effect the placement and orientation of the components of the prosthesis on the bone with the appropriate joint gaps in extension and flexion.

Considering, for example, modern knee arthroplasty, cuts are made at the distal end of the femur and proximal end of the tibia using alignment mechanisms and cutting guides. Accurate alignment of cutting guides and accurate implantation of the components of the knee prosthesis are paramount to long-term success of knee arthroplasty, both in the case of total knee arthroplasty and unicompartmental knee arthroplasty. Typically, the alignment guides are either intramedullary or extramedullary.

With intramedullary alignment guides, an intramedullary rod or similar device is placed intraoperatively in the medullary canal of the bone to be cut. Cuts to the bone are then referenced off of the intramedullary rod or off of some other device that is referenced off of a bone surface that has been cut in reference to the intramedullary rod.

With extramedullary alignment guides, an extramedullary rod or similar device is generally aligned along external landmarks to properly orient the system. For example, for resection of the proximal tibia, the extramedullary alignment guide is aligned from the center of the patient's knee to the center of the patient's ankle in a coronal plane in the medial-lateral direction. For tibial resection, the external landmarks used include the tibial tubercle, tibial spine, malleoli and foot in line with the mechanical axis of the tibia. In such procedures, the distal end of the extramedullary rod is generally affixed to the ankle through use of a clamp or similar device, such as a malleolar clamp that is positioned immediately proximal to the malleoli. A tibial resection guide is then affixed to the proximal end of the extramedullary rod. The extramedullary rod and clamping device remain external to the patient throughout the procedure. The lower assembly, comprising the clamp and the extramedullary rod, is translated in an anterior-posterior direction to align it parallel to the tibial axis. Medial-lateral alignment is adjusted to be approximately parallel to the tibial axis. Alignment of the assembly with the anatomical axis of the tibia results in proper alignment of the resection guide. The properly aligned resection guide may then be secured to the upper tibia using pins. Bone cuts may then be made to the tibia.

Refinements in topographical anatomy have resulted in a better understanding of the position of the ankle joint. Extramedullary guides are currently shifted medially at the ankle 3 to 5 mm depending on the girth of the ankle to accommodate the center of the talus. Proximal alignment of the extramedullary assembly is empirically centered between the tibial spines on the medial third of the tibial tubercle.

It is desirable that the cut to the proximal tibia, or other bone, be at a known, predetermined angle with respect to the mechanical axis of the tibia, or other bone, which in the case of the tibia, generally corresponds with the anatomical axis of the tibia. At present, there is some controversy as to whether the ultimate proximal tibial cut should be perpendicular to the tibial mechanical axis or at an angle of 3° of varus. Whichever angle is used, reproducible and accurate preparation of the upper tibia and placement of the tibial component of a knee prosthesis is extremely important for successful function and implant longevity. Proper alignment is perhaps more significant in the case of a unicompartmental or unicondylar tibial component of a knee prosthesis than in the case of a bicondylar tibial components, which are much more forgiving of malalignment than unicondylar knee prostheses. Proper alignment is also significant in the case of other joint replacement surgeries, such as in the case of shoulder prostheses and ankle prostheses.

Accordingly, to ensure that the cut made is optimal for proper alignment of the prosthetic implant with respect to an axis of the bone, it is important that the cutting guide be optimally aligned with respect to this axis of the bone. The present invention addresses the need for optimizing alignment of the surgical instruments prior to making a cut to the bone.

Reference is made to the following publications, which are incorporated by reference herein:

Teter, K. E. et al.: Accuracy of Intramedullary Versus Extramedullary Tibial Alignment Cutting Systems in Total Knee Arthroplasty. CORR 321: 106–110, 1995.

Sanders, R. et al.: Exposure of the Orthopaedic Surgeon to Radiation. JBJS 75-A: 326–330, 1993.

Evans, P. D. et al.: Radiological Study of the Accuracy of a Tibial Intramedullary Cutting Guide for Knee Arthroplasty. JOA 10: 43–46, 1995.

Dennis, D. A. et al.: Intramedullary Versus Extramedullary Tibial Alignment Systems in Total Knee Arthroplasty. JOA 8: 43–47, 1993.

Oswald, M. H. et al.: Radiological Analysis of Normal Axial Alignment of Femur and Tibia in View of Total Knee Arthroplasty. JOA 8: 419–426, 1993.

Lonner et al.: Effect of Rotation and Knee Flexion on Radiographic Alignment in Total Knee Arthroplasties. CORR 331: 102–106, 1996.

Perillo-Marcone, A. et al.: The Importance of Tibial Alignment, JOA 15: 1020–1027, 2000.

Cates, H. E. et al.: Intramedullary Versus Extramedullary Femoral Alignment Systems in Total Knee Replacement. CORR 286: 32–39, 1993.

Kennedy, W. R R. et al.: Unicompartmental Arthorplasty of the Knee. CORR 221: 278–285, 1987.

Bert, J. M. et al.: Universal Intramedullary Instrumentation for Unicompartmental Total Knee Arthroplasty. CORR 271: 79–87, 1991.

Reed, S. C. et al.: The Accuracy of Femoral Intramedullary Guides in Total Knee Arthroplasty. JOA 12: 677–682, 1997.

Thornhill, T. S. in Goldberg, V. M. Controversies of Total Knee Arthroplasty; Unicompartmental Total Knee Arthroplasty, 7–18, Raven Press, 1991.

Krackow, K. A. in Goldbery, V. M. Controversies of Total Knee Arthroplasty; Total Knee Arthroplasty: Techniques, 989–1005, Churchhill Livingstone, 1991.

Rosenberg, G. A. in Rand, J. A. *Total Knee Arthroplasty;* Surgical Technique of Posterior Cruciate Sacrificing, and Preserving Total Knee Arthroplasty, 115–153, Raven Press, 1993.

Marmor, L. in Rand, J. A. *Total Knee Arthroplasty;* Unicompartmental Knee Replacement, 245–180, Raven Press, 1993.

Scott, R. D. in Door, L. D. Techniques in Orthopaedics; Unicompartmental Knee Replacement; Robert Brigham Unicondylar Knee surgical technique, 1–23, Aspen Publication, April, 1990.

Symposia III: Unicompartmental TKR in the Millenium in the Knee Society/AAHKS Combined Specialty Day Meeting, AAOS, San Francisco, Calif. March 2001.

U.S. Pat. No. 6,036,696 (Lambrecht, et al., 2000) entitled "Guide-Pin Placement Device and Method of Use."

U.S. Pat. No. 6,214,013 B1 (Lambrecht, et al., 2000) entitled "Method of Using a Guide-Pin Placement Device."

SUMMARY OF THE INVENTION

In one aspect, the present invention provides an extramedullary fluoroscopic alignment guide to be fixed to a bone with an anchoring member during orthopaedic surgery. Part of the bone is to be resected, and the bone has an anatomic reference and a mechanical axis. The alignment guide comprises a first portion shaped to be positioned on a patient's limb at one end of a long bone and a second portion shaped to be positioned on a patient's limb at the opposite end of the long bone. The guide further includes an elongate connecting portion extending between the first portion and the second portion. At least one of the portions includes a radiopaque material; the radiopaque material is shaped and positioned to provide a radiopaque instrument reference. At least one of the portions includes radiolucent material to allow fluoroscopic viewing of at least part of the bone so that the position of the alignment guide can be adjusted to align the radiopaque instrument reference with at least part of the bone. At least one of the portions includes an opening to receive an anchoring member for fixing the position of the alignment guide with respect to the bone. The first portion, second portion and elongate connecting portion have an overall length sufficient to extend over at least a substantial part of the length of the long bone.

In another aspect, the present invention provides a method of resecting a portion of a bone of a patient's limb to receive a prosthetic implant. The bone has a long axis and at least one anatomic reference. The method comprises providing an alignment guide having an instrument reference. The alignment guide is placed on the patient's limb. The instrument reference of the alignment guide and the bone are viewed fluoroscopically simultaneously. The position of the alignment guide is adjusted so that the instrument reference is in a desired position with respect to the anatomic reference. A plurality of anchoring members are set through the alignment guide percutaneously into the bone. A portion of the bone is cut with the position of the cut being referenced from the positions of the anchoring members.

In another aspect, the present invention provides a method of resecting a portion of a bone of a patient's limb to receive a prosthetic implant. The bone has a long axis and at least one anatomic reference. The method comprises providing an alignment guide having an instrument reference. The alignment guide is placed on the patient's limb. The instrument reference of the alignment guide and the bone are simultaneously viewed fluoroscopically. The position of the alignment guide is adjusted so that the instrument reference is in a desired position with respect to the anatomic reference. The alignment guide is stabilized in the desired position, and a portion of the bone is cut with the position of the cut being referenced from the position of the alignment guide.

BRIEF DESCRIPTION OF THE DRAWINGS

In the accompanying drawings, five embodiments of the alignment guide of the present invention are illustrated. In these drawings, like reference numbers have been used for like parts, and:

FIG. 1 is a top plan view of a first embodiment of the extramedullary fluoroscopic alignment guide of the present invention;

FIG. 2 is a side view of the extramedullary fluoroscopic alignment guide of FIG. 1;

FIG. 3 is a perspective view of the bottom side of the extramedullary fluoroscopic alignment guide of FIGS. 1 and 2;

FIG. 3A is a plan view of an extramedullary fluoroscopic alignment guide of the type shown in FIGS. 1–3, shown with modular handles in place;

FIG. 3B is a top plan view of a second embodiment of the extramedullary fluoroscopic alignment guide of the present invention;

FIG. 4 is a top plan view of a third embodiment of the extramedullary fluoroscopic alignment guide of the present invention, with the telescoping parts of the connecting portion in a fully retracted position;

FIG. 5 is a side view of the extramedullary fluoroscopic alignment guide of FIG. 4, with the telescoping parts of the connecting portion in a fully retracted position;

FIG. 19 is a perspective view of the two-piece first portion of the guide of FIGS. 15–18;

FIG. 20 is a perspective view of an alternate first portion for the guide of FIGS. 15–18, with the top portion being a single integral piece;

FIG. 21 is a top plan view a the top piece of the first portion shown in FIG. 19;

FIG. 22 is a side elevation of the top piece of the first portion shown in FIGS. 19 and 21;

FIG. 23 is a bottom plan view of the top piece of the first portion shown in FIGS. 19 and 21–22;

FIG. 24 is a cross-section of the top-piece of FIGS. 19 and 21–23, taken along line 24—24 of FIG. 22;

FIG. 25 is an elevation of one telescoping part of the connecting portion of the guide of FIGS. 4–8 and 13–18;

FIG. 26 is an elevation of the part of FIG. 25, rotated 90°;

FIG. 30 is a perspective view of the body of the two-piece proximal or first portion of the guide of FIGS. 15–17;

FIG. 31 is a bottom plan view of the body of FIG. 30;

FIG. 32 is a perspective view of the distal piece of the connecting portion of the guide of FIGS. 15–18;

FIG. 33 is a cross-section of the distal piece of FIG. 32, taken along line 33—33 of FIG. 32;

DETAILED DESCRIPTION

In the accompanying drawings several embodiments of an extramedullary fluoroscopic alignment guide are illustrated. The first embodiment is illustrated in FIGS. 1–3 and 9 at 10A. Another embodiment is illustrated in FIG. 3B at 10B. A third embodiment is illustrated at 10C in FIGS. 4–8. Fourth and fifth embodiments are illustrated at 10D and 10E in FIGS. 13–18. These extramedullary fluoroscopic alignment guides 10A–10E are to be temporarily fixed to a bone, such as the tibia shown in phantom at 14 in FIGS. 9 and 10, during orthopaedic surgery wherein part of the bone is to be resected. The tibia 14 has an anatomic axis, shown at 16 in FIGS. 9–10, which corresponds generally with the mechanical axis of the tibia. The illustrated embodiments of the extramedullary fluoroscopic alignment guide can be aligned with the anatomic axis of the bone, and provide radiopaque instrument references that can be viewed fluoroscopically and compared to the bone, which can be viewed through radiolucent portions of the alignment guide.

The illustrated embodiments 10A–10E of the fluoroscopic alignment guide include a first portion 18A–18E, a second portion 20A–20E and a connecting portion 22A–22E. In the illustrated embodiments, the first portion 18A–18E comprises a cephalad or proximal portion and the second portion 20A–20E comprises a distal portion.

Although the illustrated embodiments, which are described below, are designed to be used as tibial alignment devices, it should be understood that the principles of the present invention may be applied to alignment devices used in other joint replacements. For example, for a shoulder joint replacement, the device may be configured for use along the patient's humerus. For ankle joint replacement, the device may be configured for cuts to be made near the distal end of the tibia rather than the proximal end, as in the following illustrated embodiments.

The proximal or cephalad portion 18A–18E of the illustrated embodiments of the fluoroscopic alignment guide 10A–10E includes a body 23A–23E with a posterior surface 24A–24E. In these illustrated embodiments, the posterior surface 24A–24E is contoured so that it may be placed against an exterior surface of the patient's knee, with some stability against undesired motion. In the illustrated embodiments, the posterior surface 24A–24E is curved. The posterior surface 24A–24E may be contoured to conform roughly to the inferior pole of the patella and the patella tendon.

Figure 11:
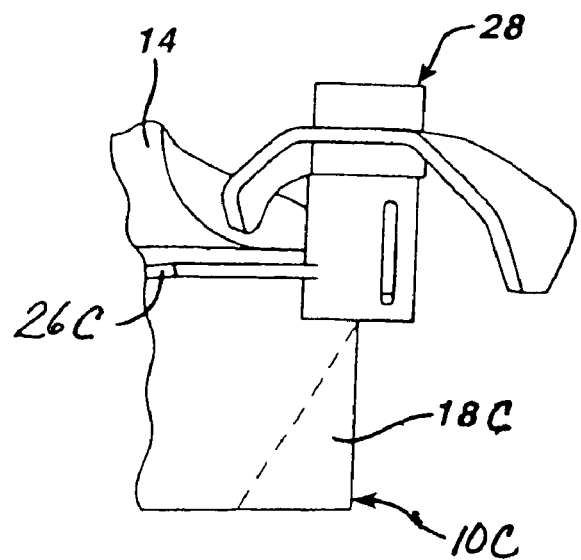
FIG. 11 is a perspective illustration of a stylus mounted on the proximal portion of the embodiment of the alignment guide of FIGS. 4–8.
Figure 12:
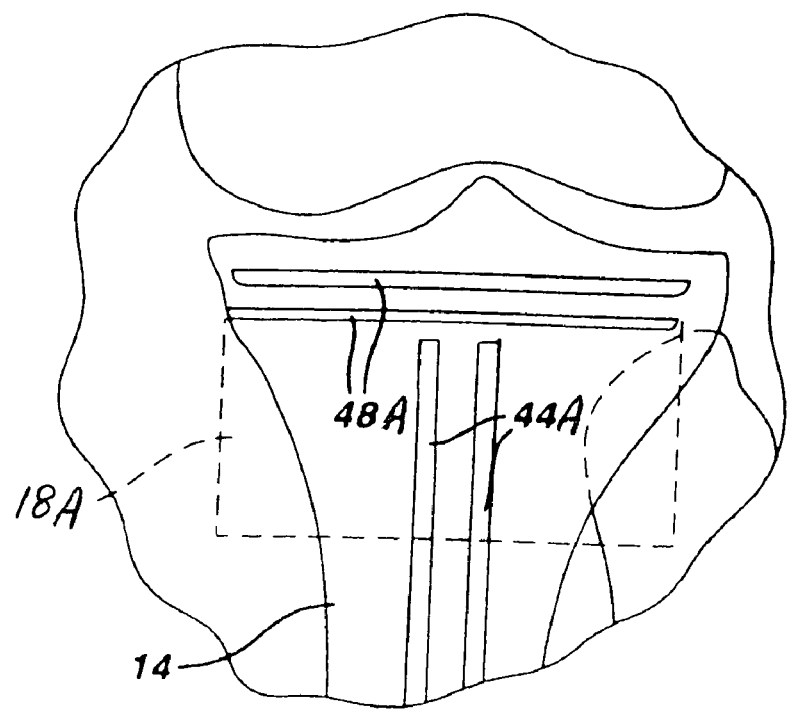
FIG. 12 is a schematic illustration of a radiograph illustrating the position of the radiopaque instrument reference wires of the first illustrated embodiment overlying the patient's bone.

The body 23C of the cephalad or proximal portion 18C of the alignment guide 10C illustrated in FIGS. 4–8 also includes a plurality of spaced openings. One opening comprises an elongate transverse slot 26 in the anterior surface 27 that is provided to receive the foot of a tibial stylus 28 as shown in FIG. 11. The tibial stylus 28 used may be a conventional one. Another set of openings in the embodiments 10C, 10D, 10E of FIGS. 4–8 and 13–18 are circular, and are provided to receive anchoring members. These circular openings 30C, 30D, 30E are through openings, and extend from the anterior surface 27C, 27D, 27E to the posterior surface 24C, 24D, 24E of the body 23C, 23D, 23E of the first portion 18C, 18D, 18E. Each of the circular openings 30C in the embodiment of FIGS. 4–8 has a central longitudinal axis that extends in a generally anterior-posterior direction when the alignment guide is placed on the patient. In the embodiments 10C, 10D, 10E illustrated in FIGS. 4–8 and 13–18, these central longitudinal axes of these circular holes are generally about 10° off from a sagittal plane through the openings, as shown in the cross-section of FIG. 24. The angular orientation of the circular holes may generally correspond to the angular orientation of the holes in the cutting block that will subsequently be placed over the anchoring members, if a separate cutting block is used. For embodiments where the alignment guide also serves as a cutting guide, the angular orientation of the holes 30D, 30E relative to a sagittal plane through provides mechanical stability through cross-pinning. Generally, the circular openings 30C in the embodiment of FIGS. 4–8 are arrayed in a pattern that is the same as the pattern of pin holes in the cutting guide that will be used. It should be understood that the invention is not limited to any particular pattern of circular holes or to exact correspondence with the pin holes of the cutting block; for example, the alignment guide of the embodiment illustrated in FIGS. 4–8 could be used with a cutting block that has one or more cross-pinning holes for stabilization.

The anchoring members may comprise standard metal pins commonly used in arthroplasty, such as Steinmann pins, or drill bits. Examples of anchoring members are shown at 32 in FIGS. 9–10. Generally, the anchoring members 32 may be set in the bone 14 as in standard arthroplasty procedures, and, in some embodiments of the invention, the alignment guide 10A, 10B, 10C may be slipped off of the anchoring members 32 while the anchoring members 32 remain secured to the bone 14. As described more fully below, and as shown for example in FIG. 10, a cutting guide may then be slid over these anchoring members 32, and thereby be fixed in a position defined by the anchoring members. An example of a cutting guide is shown at 34 in FIG. 10. Thus, the position of the cephalad portion 18A, 18B, 18C and the overall alignment of the fluoroscopic alignment guide 10A, 10B, 10C may be translated to the cutting guide 34 for proper resection of the proximal tibia 14. Alternatively, the alignment guide could be secured and cuts made directly using the alignment guide as a guide to guide the position and orientation of the cutting tool; the embodiments 10D and 10E of FIGS. 13–18 may be so used.

Figure 6:
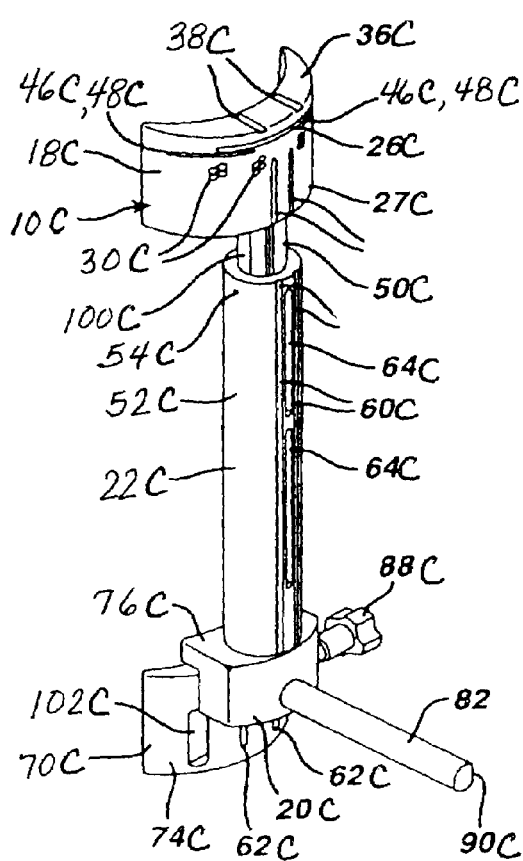
FIG. 6 is a perspective view of the extramedullary fluoroscopic alignment guide of FIGS. 4–5, taken from the top of the device and showing the telescoping parts of the connecting portion in the fully retracted position.
Figure 7:
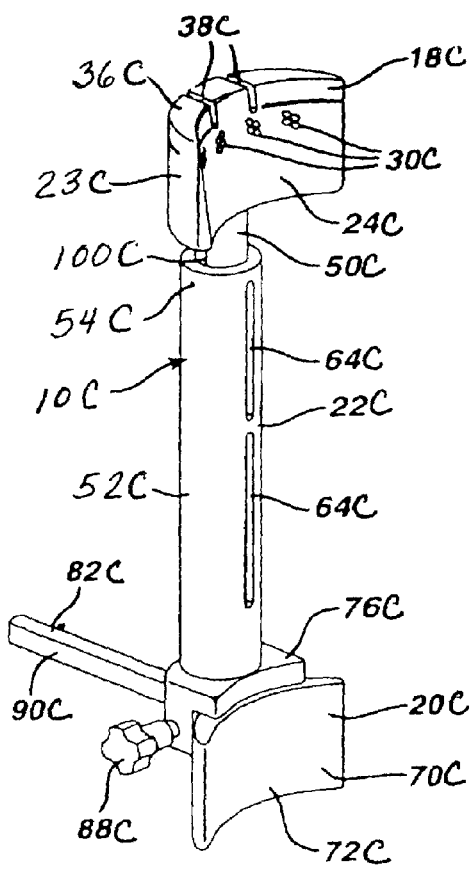
FIG. 7 is a perspective view of the extramedullary fluoroscopic alignment guide of FIGS. 4–6, showing the telescoping parts of the connecting portion in the fully retracted position.
Figure 8:
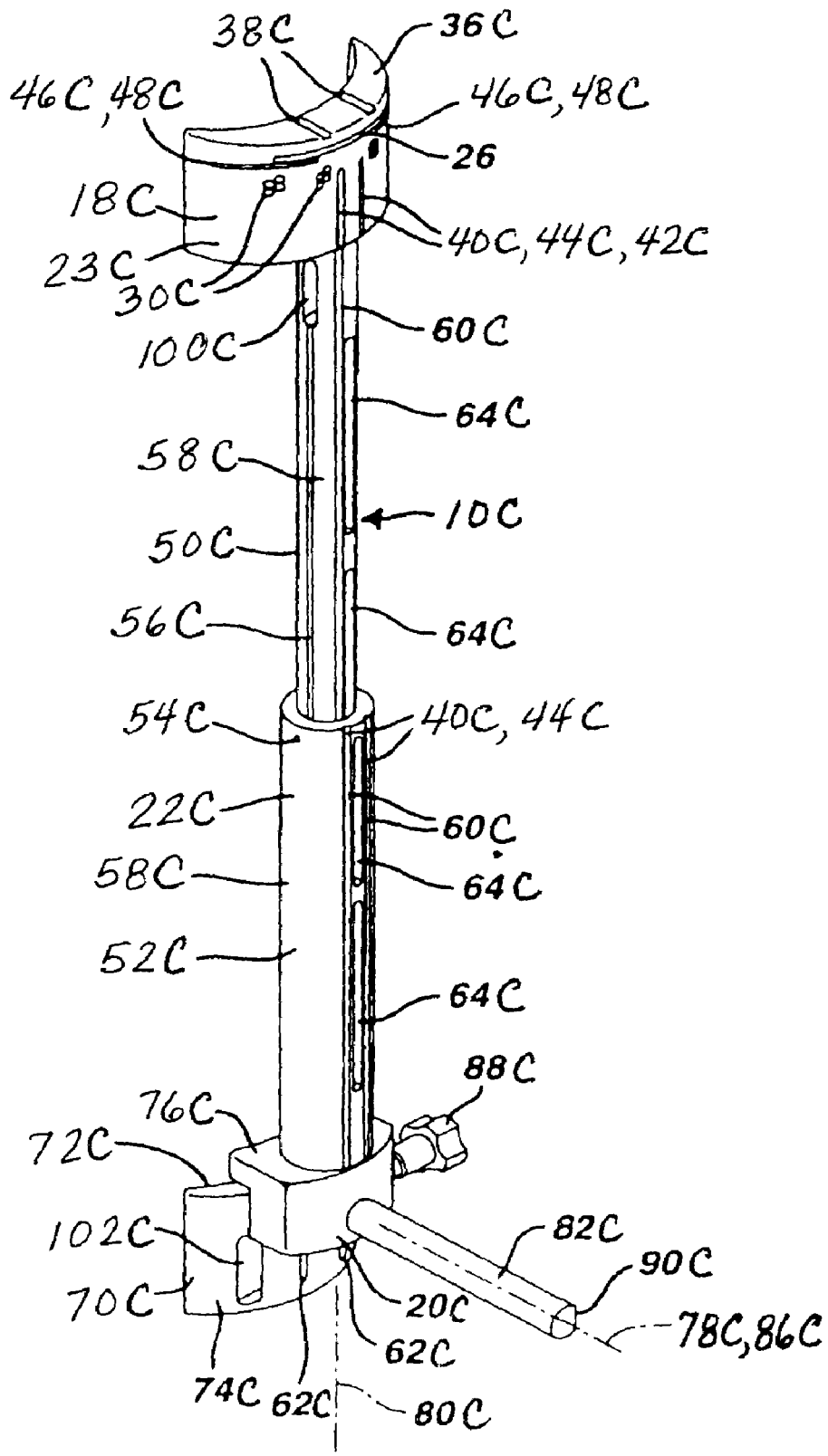
FIG. 8 is a perspective view of the extramedullary fluoroscopic alignment guide of FIGS. 4–7, shown with the telescoping parts of the connecting portion in a fully extended position.

The body 23A–23E of the cephalad portion 18A–18E of the fluoroscopic alignment guide in the illustrated embodiments of alignment guides 10A–10E includes a transverse top surface 36A–36E. The transverse top surface 36A, 36C of the alignment guides 10A, 10C illustrated in FIGS. 1–3A and 4–8 includes at least one anterior-posterior groove 38A, 38C. The first illustrated alignment guide 10A has a single groove 38A and the alignment guide 10C has two such grooves 38C, as shown in FIGS. 6–7. These grooves 38A, 38C may provide a visual reference for the surgeon to establish the internal/external rotation for the guide and therefore the tibial cut.

To be able to set the position of the cephalad or proximal portion 18A–18E of the fluoroscopic alignment guide relative to anatomic landmarks, the body 23A–23E of the cephalad portion 18A–18E includes a radiolucent material. Generally, a substantial part of the body 23A–23E comprises radiolucent material in the illustrated embodiments. Thus, the bone 14 and anatomic landmarks can be seen fluoroscopically during surgery. To provide an instrument reference during fluoroscopy, the cephalad portion 18A–18E may also include a radiopaque material. The radiopaque material in the illustrated embodiments is shown at 40A–40E and comprises thin stainless steel wires. In the illustrated embodiments, stainless steel wire with a diameter of 3/32 inches can be used, although it should be understood that the present invention is not limited to any particular material or dimension of material unless expressly called for in the claims. For example, higher density corrosion resistant material, such as tantalum, could be used.

In the embodiments 10A–10C of FIGS. 1–8, the fluoroscopic alignment guides' two radiopaque wires 40A–40C are received in a pair of spaced longitudinal grooves 42A–42C that provide radiopaque longitudinal instrument references 44A–44C that are visible fluoroscopically. The first illustrated alignment guide 10A has transverse grooves (not shown) through the proximal body 18 to receive a radiopaque material to provide a pair of radiopaque transverse instrument references that are visible during fluoroscopy. The alignment guide 10C illustrated in FIGS. 4–8 also includes transverse grooves 46C in the anterior surface of the body 23C of the cephalad portion 18C that receive a radiopaque material to provide a pair of radiopaque transverse instrument references 48C that are visible during fluoroscopy. In the embodiments of FIGS. 13–18, the radiopaque longitudinal references 44D, 44E are provided by radiopaque wires 40D, 40E received in bores in the first and second portions 18D, 18E, 20D, 20E of the alignment guide 10D, 10E. The radiopaque longitudinal instrument references 44A–44E in the illustrated alignment guides 10A–10E allow the surgeon to visualize the position of these instrument references 44A–44E with respect to anatomic landmarks, such as the mechanical axis of the bone. The transverse instrument reference 48C in the third embodiment 10C, the transverse instrument reference (not shown) in the first embodiment, and T-shaped transverse radiopaque instrument reference 49 in the embodiment 10B of FIG. 3B allow the surgeon to visualize the position of these instrument references 48C, 49 with respect to an anatomic landmark such as the condylar line of the tibia. As discussed below, a radiopaque transverse instrument reference could also be provided by a separate tool, such as a slope guide, that is removably attached to the alignment guide 10D, 10E. Based on the fluoroscopic images, the surgeon can adjust the position of the alignment guide 10A–10E until the radiopaque instrument references 44, 48C 49 are in the desired position relative to the anatomic landmarks.

In the illustrated embodiments, the proximal or cephalad portion 18A–18E of the alignment guide 10A–10E is attached to at least a part of the connecting portion 22A–22E of the alignment guide 10A–10E. In the embodiments of the fluoroscopic alignment guide 10A, 10B illustrated in FIGS. 1–3B, the connecting portion 22A, 22B comprises a single elongate piece of radiolucent material that is formed integral with both the proximal portion 18A, 18B and distal portion 20A, 20B of the alignment guide 10A, 10B. In the embodiment of the fluoroscopic alignment guide 10C illustrated in FIGS. 4–8, the connecting portion 22C comprises two independent pieces 50C, 52C. One piece 50C is formed integral with the proximal or cephalad portion 18C and the other piece 52C is integral with the second or distal portion 20C. In the embodiments of FIGS. 13–18, the first and second portions 50D, 50E, 52D, 52E are discrete elements secured to the other portions 18D, 18E, 20D, 20E. However, it should be understood that other designs are possible and are within the scope of the invention. For example, the connecting portion could include a rod or similar element received within a mating slot in the cephalad portion, or the cephalad portion could include a part that is received within a mating opening in the connecting portion, and allowing controlled relative movement between the portions.

In the fluoroscopic alignment guides 10C–10E illustrated in FIGS. 8–18, one of the independent pieces 50C–50E of the connecting portion is received within the other independent piece 52C–52E in a telescoping fashion so that the length of the connecting portion 22C–22E can be adjusted as desired. The provision of an adjustable length allows the alignment guide 10C–10E to be adjusted to span the length of the tibia from the knee to the ankle for patients of different sizes. In these embodiments, the outer sleeve part 52C–52E includes a pair of dowel pins 54C–54E that extend inward and contact elongate slots 56C–56E in the outer surface of the inner arm part 50C–50E of the connecting portion 22C–22E. These dowel pins 54C–54E serve to prevent relative rotation of the two parts 50C–50E, 52C–52E. A ball plunger, O-ring (not shown) or other device may be provided to limit relative longitudinal movement so that the parts 50C–50E, 52C–52E do not slide undesirably in use.

The connecting portions 22A–22E of the illustrated embodiments of the fluoroscopic alignment guide 10A–10E include radiolucent material, and include an outer surface 58A–58E. The first three embodiments 10A–10C include longitudinal grooves 60A–60C in the outer surface 58A–58C. These longitudinal grooves 60A–60C are parallel to each other and are aligned to be co-linear with the longitudinal grooves 42A–42C of the cephalad portion 18A–18C. Each longitudinal groove 60A–60C in the illustrated embodiments receives one or more elongate stainless steel wires that serves as part of the radiopaque longitudinal instrument reference 44A–44C. When the surgeon views the alignment device 10A–10C on the patient fluoroscopically, the surgeon will be able to see a substantial part of the patient's tibia, including anatomic landmarks, as well as the long thin lines of the radiopaque longitudinal instrument references 44A–44C. From an anterior fluoroscopic view, the surgeon will be able to align the alignment device 10A–10C in the medial-lateral direction to an optimal position based on anatomic landmarks viewed simultaneously with the radiopaque instrument references. Additionally, the radiopaque transverse instrument reference 47 of the second embodiment 10B can be viewed fluoroscopically aligned in the sagittal plane to the slope of the patient's native tibia.

Figure 9:
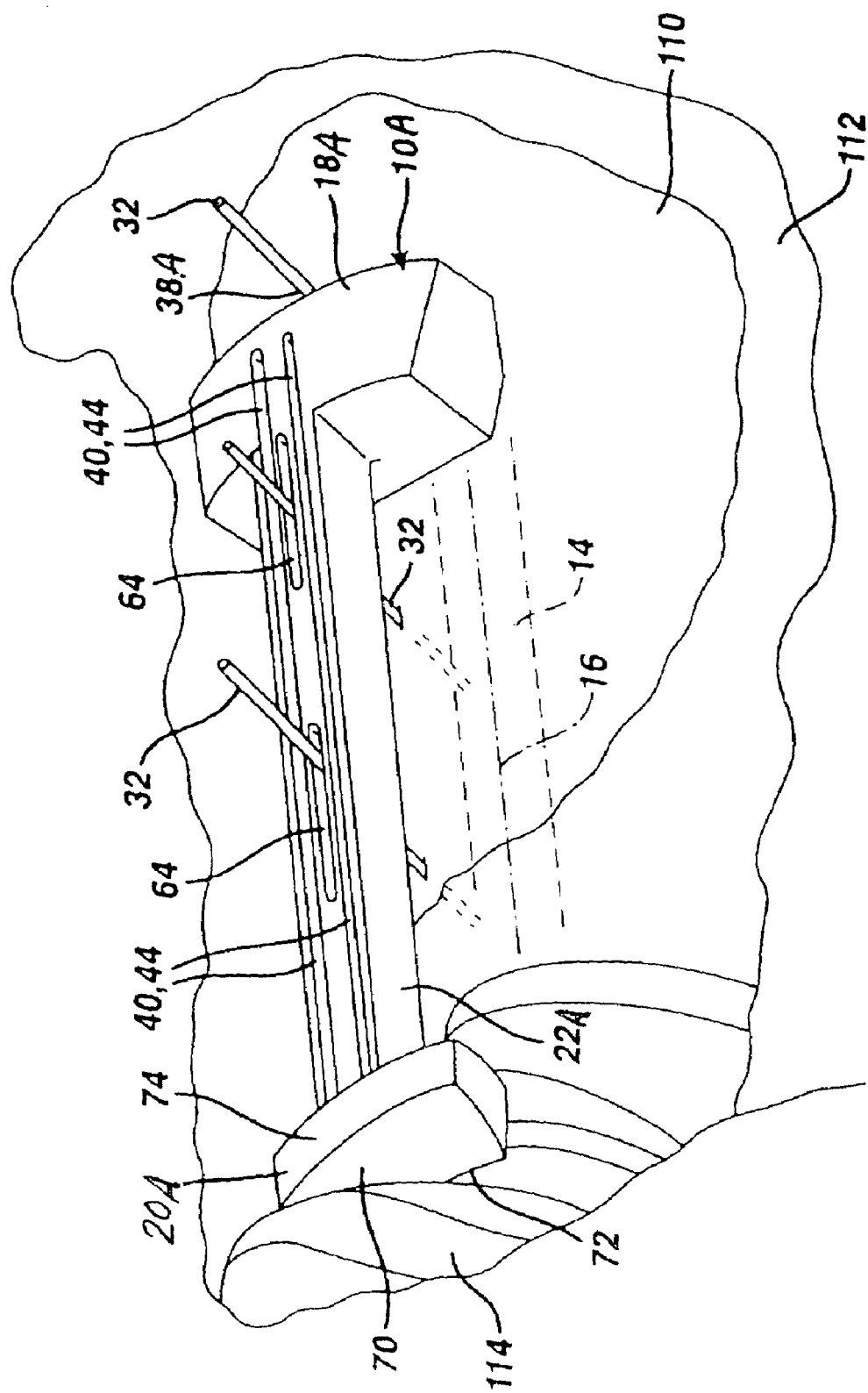
FIG. 9 is a perspective illustration of the extramedullary fluoroscopic alignment guide of FIGS. 1–3, shown on the outside anterior surface of a leg of a patient, with Steinmann pins set through the alignment guide and into the patient's tibia.

The connecting portions 22A–22E of all the illustrated fluoroscopic alignment guides 10A–10E include a plurality of through-openings 64A–64E that are open in an anterior-posterior direction through the connecting portions 22A–22E. These openings 64A–64E are suitable to receive anchoring members 32, such as Steinmann pins or drill bits, as shown in FIG. 9. Thus, when the surgeon determines that the fluoroscopic alignment device 10A–10E is properly oriented in the medial-lateral direction, the surgeon may place the anchoring members 32 to fix the position of the alignment device 10A–10E. Assuming that the cephalad portion 18A, 18B is in the proper position relative to the tibial condyles, the cephalad portion 18A, 18B may also be fixed in position by placing anchoring members 32 through the circular through holes 30A, 30B in the cephalad portion 18A, 18B of the alignment guide 10A, 10B of FIGS. 4–8 and in the grooves 38A, 38C in the top surface 36A, 36C of the cephalad portion 18A, 18C of either embodiment illustrated in FIGS. 1–3A and 4–8. The alignment device 10A, 10B maybe removed while leaving the anchoring members 32 in place by lifting the device 10A, 10B.

It should be understood that although the through openings 64A–64E in the connecting portion 22A–22E may be aligned with the circular openings 30A–30E in the proximal or cephalad portion 18A–18E, they need not be. As discussed above, the central longitudinal axes of the circular openings 30A–30E in the proximal or cephalad portion 18A–18E may be set at an oblique angle if the alignment guide is to be used with a cutting guide or block that uses oblique pins, or if the alignment guide is to also serve as a cutting guide.

In the illustrated embodiments, the through openings 64A–64E in the connecting portion 22A–22E comprise spaced elongate slots along the center of the connecting portion. These slots 64A–64E are about ⅛-inch wide; in the first three embodiments, these slots 64A–64C extend between the grooves 60A–60C that receive the longitudinal radiopaque reference wires 44A–44C. It should be understood that the openings 64A–64C could comprise a plurality of smaller holes. In addition, it should be understood that the invention is not limited to guides that include openings in both the connecting portion 22A–22E and cephalad portion 18A–18E unless expressly set forth in the claims. Moreover, as discussed below with respect to the fourth and fifth embodiments 10D, 10E, the connecting portion 22D, 22E need not carry any radiopaque material.

In the fluoroscopic alignment guides 10C–10E of FIGS. 4–8 and 13–18, there are through holes 64C–64E in both of the telescoping pieces 50C–50E, 52C–52E of the connecting portion 22C–22E. These through holes 64C–64E may be aligned so to provide an open anterior-posterior path for the anchoring devices 32.

The distal portion 20A, 20B in the fluoroscopic alignment guide 10A, 10B of FIG. 3 and FIG. 3B comprises a body 70A, 70B of radiolucent material that is integral with the connecting portion 22A, 22B. The body 70A, 70B includes a posterior surface 72A, 72B and an anterior surface 74A, 74B. The posterior surface 72A, 72B bears against a portion of the patient's body either directly or through a wrapping or other structure, and preferably is generally contoured to abut an anterior surface of the patient's body or wrapping. As shown in FIG. 3, the posterior surface 72A of the distal portion 20A is preferably curved so that it may be placed against the anterior exterior surface of the patient's ankle in a relatively stable position. The posterior surface may be contoured to conform roughly with the anterior crest of the tibia ending near the ankle.

In the alignment guide 10C illustrated in FIGS. 4–8, the distal portion 20C includes a pair of grooves 62C in the anterior surface that are aligned with the longitudinal grooves 60C on the connecting portion 22C. These grooves 62C in the distal portion 20C extend generally to the ankle of the patient. The grooves 62C contain a radiopaque material to extend the longitudinal radiopaque instrument reference 44C to the patient's ankle. Such extended or additional grooves could be provided in the first illustrated alignment guide 10A as well. In the alignment guides 10D, 10E of FIGS. 13–18, radiopaque material is carried within bores in the interior of the body of the second or distal portion 20D, 20E of the alignment guide.

In the embodiments of alignment guides 10A, 10B illustrated in FIGS. 1–3A and FIG. 3B, the distal portion 20A, 20B is integral with the connecting portion 22A, 22B. In the alignment guides 10C–10E illustrated in FIGS. 4–8 and 13–18, the distal portion 20C–20E comprises a separate element that is removably attached to the distal end 76C–76E of the connecting portion 22C–22E of the alignment guide 10C–10E. The connection between these two elements 20C–20E, 22C–22E allows relative movement between the distal portion 20C–20E and the connecting portion 22C–22E along an axis 78C–78E that is generally perpendicular to the longitudinal axis 80C–80E of the connecting portion 22C–22E. To provide this relative motion, the distal portion 20C–20E of the alignment guide 10C–10E of FIGS. 4–8 and 13–18 includes a rod 82C–82E extending outward from the anterior surface 74C–74E of the body 70C–70E. This rod 82C–82E is received in an opening 84C–84E, at the distal end piece 76C–76E of the connecting portion 22C–22E. In the illustrated embodiments, the opening 84C–84E has a longitudinal axis 86C–86E that is generally perpendicular to the longitudinal axis 80C–80E of the connecting portion 22C–22E. The rod 82C–82E can slide in the mating opening 84C–84E relative to the connecting portion 22C–22E, in a direction perpendicular to the central longitudinal axis 80C–80E of the connecting portion 22C–22E. The illustrated design may be modified, for example, by making element 82C–82E curved and changing the shape of the opening 84C–84E to provide extra clearance to allow curvilinear motion; thus, the assembly can pivot about the proximal portion while the distal end 76C–76E of the connecting portion 22C–22E moves away from the body 70C–70E of the distal portion 20C–20E of the guide. Such pivoting can also be achieved using the design shown in FIG. 33. As shown in FIG. 33, the opening 84E is not symmetrical about axis 86E; instead, the top of the interior wall angles upward at the anterior end and then straightens at the posterior end, while the bottom of the interior wall is straight at the anterior end and angles downward at the posterior end. With the opening 84E shaped as shown in FIG. 33, relative rocking or pivoting is possible between the second portion 20E and the connecting portion 22E of the alignment guide. The distal end piece 76C–76E of the connecting portion 22C–22E in the illustrated embodiments 10C–10E includes a locking mechanism 88C–88E comprising a threaded set screw that bears against a flat surface 90C–90E of the rod 82C–82E to set the position of the distal portion 20C–20E in an anterior-posterior direction. Thus, the surgeon can view a fluoroscopic image of the leg taken from a medial or lateral perspective and align the transverse radiopaque instrument reference 48C, 159 with the native posterior tibial slope. From this perspective, the surgeon can also view the angular relationship between the longitudinal radiopaque reference instrument references 44C–44E and the anatomic axis 16 of the tibia 14. The slope can be adjusted by sliding the distal end piece 76C–76E of the connecting portion 22C–22E relative to the distal portion 20C–20E of the alignment guide 10C–10E until the surgeon is satisfied with the angular position of the alignment guide 10C–10E relative to anatomic landmarks.

Figure 13:
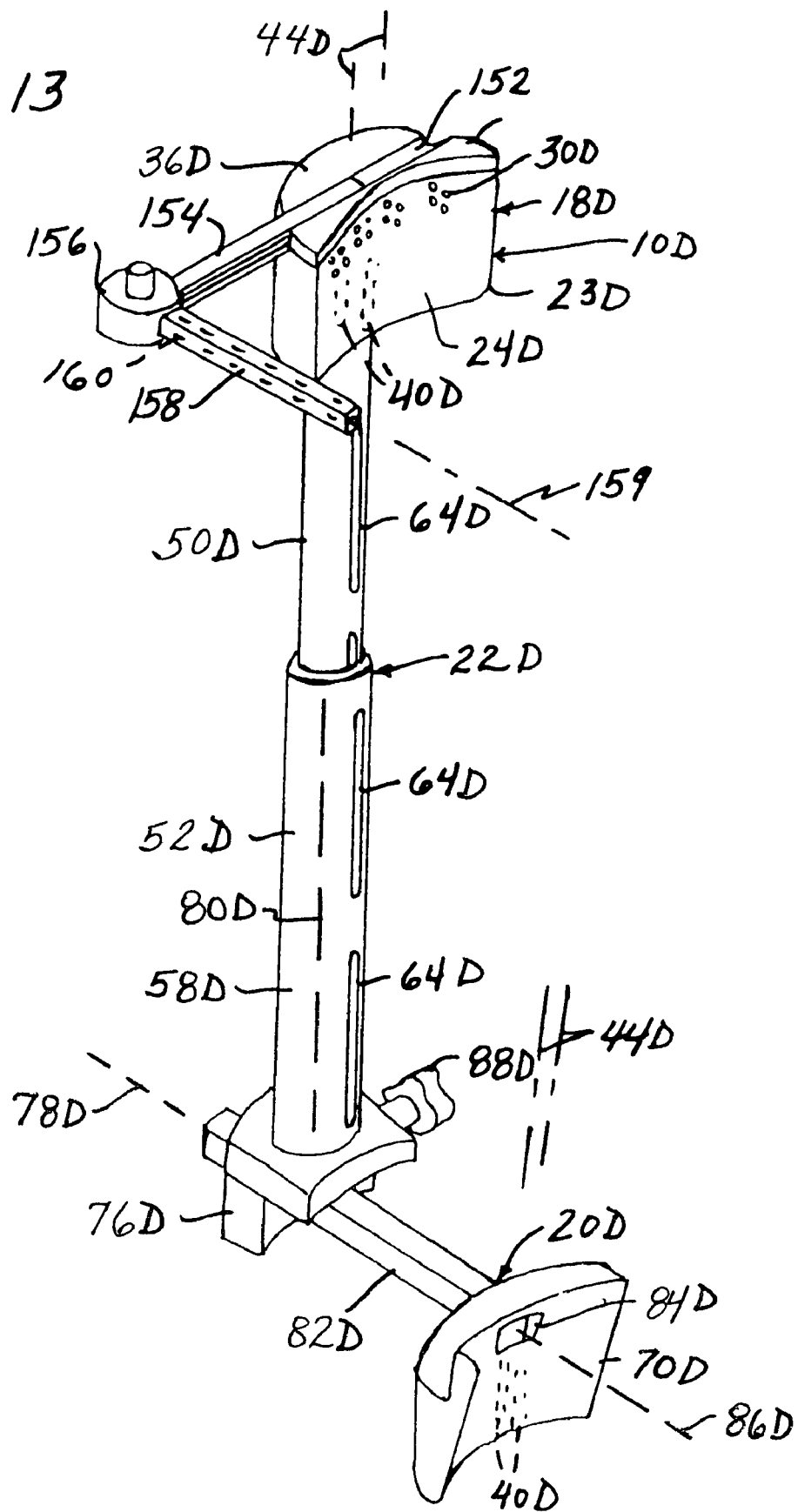
FIG. 13 is a perspective view of a fourth embodiment of the extramedullary fluoroscopic alignment guide of the present invention, shown with a slope guide carried by the first portion of the guide.
Figure 14:
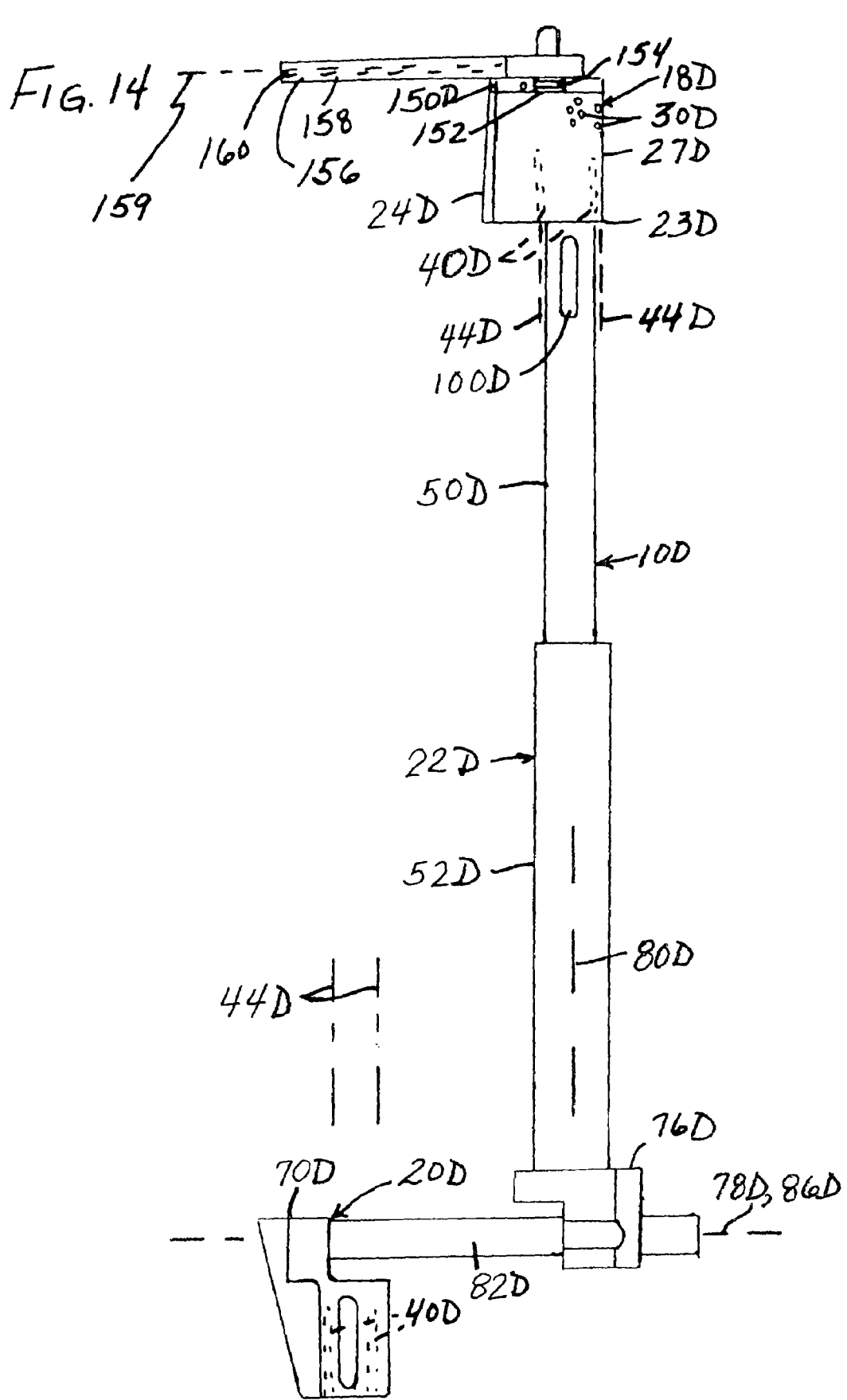
FIG. 14 is a side elevation of the embodiment of FIG. 13.

When using the fluoroscopic alignment guide 10C of FIGS. 4–8, the surgeon can view the patient's tibia from a medial or lateral perspective, and can also view the transverse radiopaque instrument reference 48C provided by the transverse radiopaque material in the cephalad portion 18C of the fluoroscopic alignment guide 10C. The radiopaque transverse instrument reference 48C in the embodiment of FIGS. 4–8 is curved so that the transverse instrument reference line 48C is visible from both the anterior perspective and from the medial and lateral perspectives. Other alternative configurations may be used for the illustrated embodiments. For example, transverse radiopaque instrument references could be provided that extend in an anterior-posterior direction; the slope of such posteriorly-directed transverse references could then be compared fluoroscopically to the posterior slope of the patient's native tibial plateau. FIG. 3B illustrated an alignment device with a T-shaped transverse radiopaque instrument reference 47, part of which, shown in phantom at 49, extends in an anterior-posterior direction; such a radiopaque instrument reference could be used in the other illustrated embodiments as well. Another alternative is illustrated in FIGS. 13–14: a radiopaque transverse instrument reference could by provided by a separate tool mountable to the alignment guide, as in the slope guide discussed below with respect to the embodiments of FIGS. 8–13. It should be understood that the transverse instrument reference could be provided in a groove in the posterior surface of the proximal portion, or be embedded within the body of the proximal portion. The visibility provided by the transverse radiopaque instrument references allows for further fluoroscopic evaluation of the position of the alignment guide prior to cutting the bone.

It should be understood that other structures may be used for the distal portion of the alignment guide. For example, a malleolar clamp may be used. Preferably, for a tibial alignment guide, the device at the distal end will allow for anterior-posterior adjustments so that the desired slope of the tibial resection may thereby be adjusted. Other devices which accomplish this result may be used, as well as separate devices that are used with an alignment guide.

In the illustrated embodiments, the distal portion 20A–20E is made of a radiolucent material, like the proximal portion 18A–18E and connecting portion 22A–22E. Although it is possible that the distal portion could be made of a material that is not radiolucent, use of a radiolucent material is preferred so that the surgeon can fluoroscopically image the ankle and align the guide 10A–10E to the medial-lateral center of the ankle.

In the embodiment of FIGS. 13–14, the first proximal portion 18D comprises an assembly of two parts, the body 23D and a top member 150D. The body 23D is made of a radiolucent material, and includes the circular openings 30D to receive anchoring members, as in the embodiment of FIGS. 4–8. The body 23D also includes radiopaque material in the form of wires 40D serving as radiopaque longitudinal references 44D.

In the embodiment of FIGS. 13–14, the top member 150D of the first proximal portion 18D is formed of a different material than the body 23D, and comprises metal such as anodized aluminum or stainless steel in the illustrated embodiment. The use of metal may be desirable for durability, since as described below, the top member 150D can be used for mounting tools to the alignment guide and can also be used for a cutting guide. However, it should be understood that the top member 150D could be formed of other materials, such as a polymer, and the invention is not limited to a particular material or to material with particular characteristics for the top member 150D unless expressly called for in the claims.

In the embodiment of FIGS. 13–14, the top member 150D has a transverse medial-lateral slot 152 formed therein to receive a mounting arm 154 of a removable slope guide 156 tool. In the embodiment shown in FIGS. 13–14, the slot 152 extends across the entire medial-lateral dimension of the top member 150D although two slots 153, 155 could be used, one extending from the medial edge and one extending from the lateral edge of the top member 150E, as in the embodiments of FIGS. 15–18.

Figure 37:
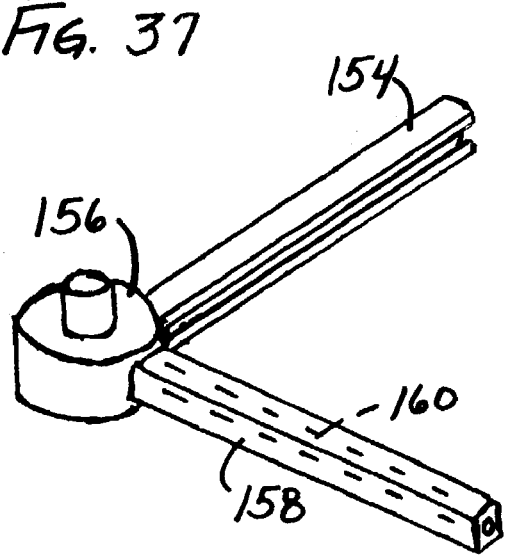
FIG. 37 is a perspective view of a slope guide that can be mounted on the guide of FIGS. 13–18.

The illustrated removable slope guide tool 156 also includes a slope guide arm 158 joined to the mounting arm 154. The slope guide arm 158 includes radiopaque material along its length to provide a radiopaque transverse instrument reference 159. The radiopaque material, such as a metal wire 160 (see FIG. 37), of the slope guide arm 158 runs perpendicular to the radiopaque longitudinal instrument reference 44D, 44E and provides an anterior-posterior transverse radiopaque reference when the patient's leg is viewed fluoroscopically from a medial or lateral perspective. The mounting arm 154 of the slope guide 156 can be inserted into the transverse slot 152D, 153, 155 of the top member 150D, 150E either from the medial or lateral side. With the slope guide 156 in position, the surgeon can set the slope of the alignment guide 10D, 10E in the sagittal plane by aligning the radiopaque wire 160 with the native slope of the patient's tibia, or with some other reference the surgeon desires to use that is visible from either a medial or lateral perspective. The top 36D, 36E surface of the top member 150D, 150E may also serve as a cutting guide so that the surgeon can cut directly off of the alignment guide 10D, 10E rather than removing the alignment guide and placing a separate cutting guide on the anchoring devices 32.

In the embodiment of FIGS. 15–18, the first proximal portion 18E also comprises an assembly of two parts, the body 23E and top member 150E. The assembly of the body 23E and top member 150E is shown in FIG. 19. As shown in FIG. 20, the body 23E and top member 150E could be made as a single, integral part.

Figure 15:
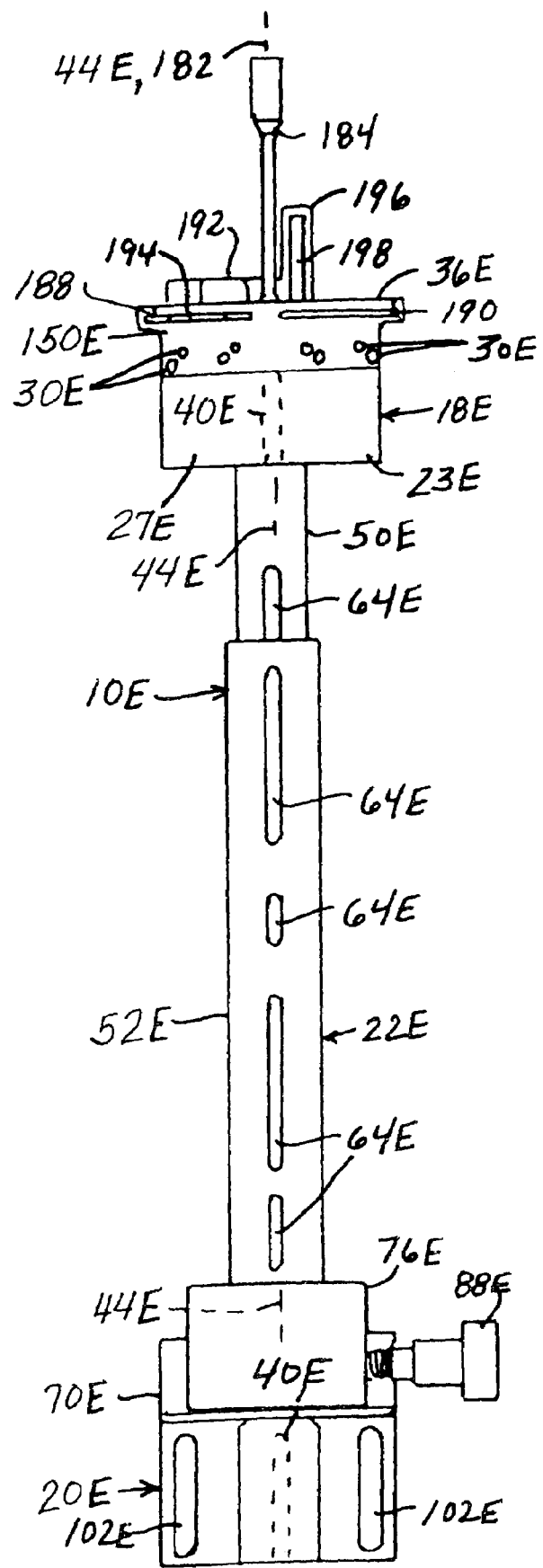
FIG. 15 is a top plan view of a fifth embodiment of the extramedullary fluoroscopic alignment guide of the present invention, shown with a radiopaque reference extender carried by the top portion of the guide.
Figure 16:
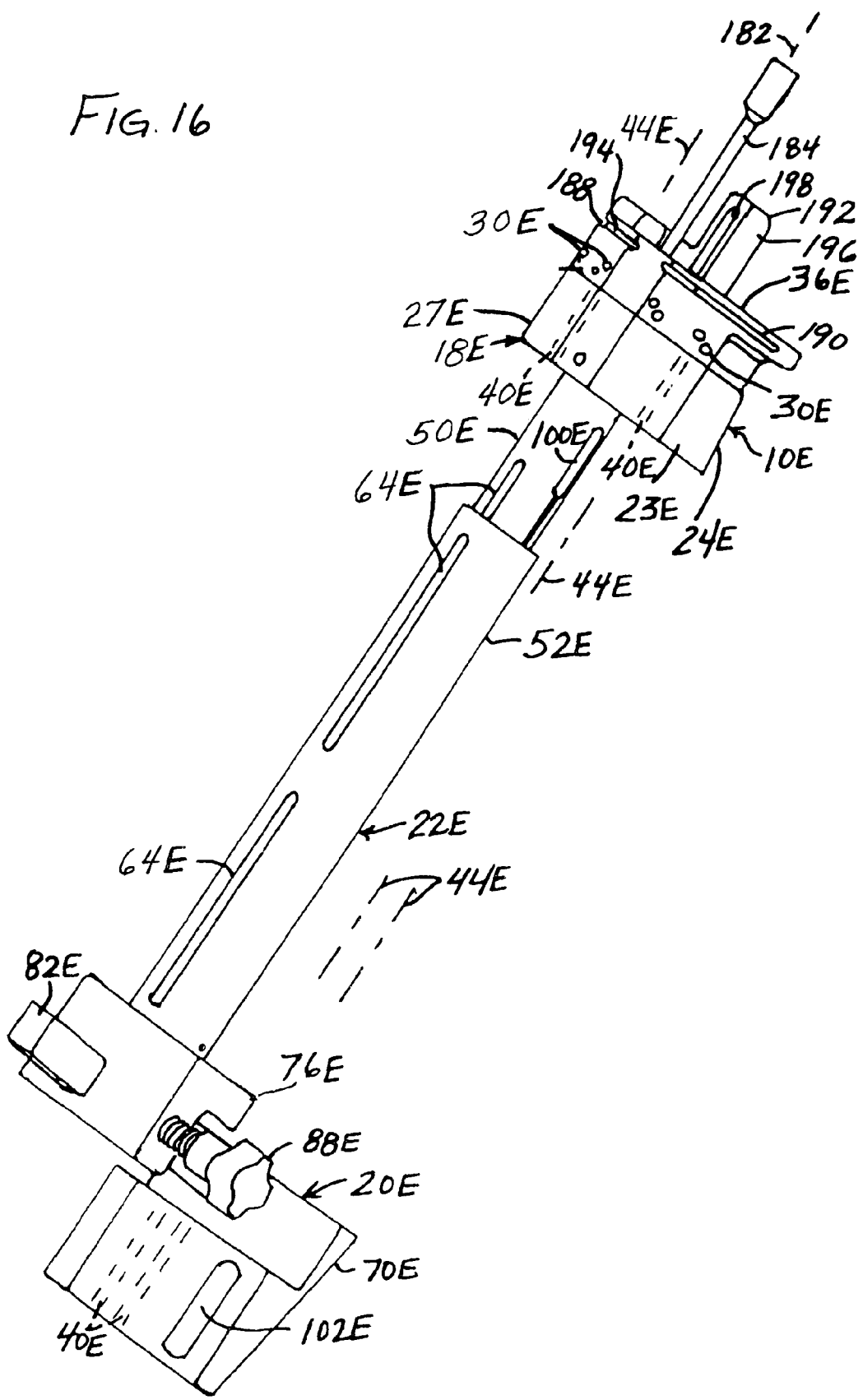
FIG. 16 is a side elevation of the embodiment of FIG. 15.
Figure 17:
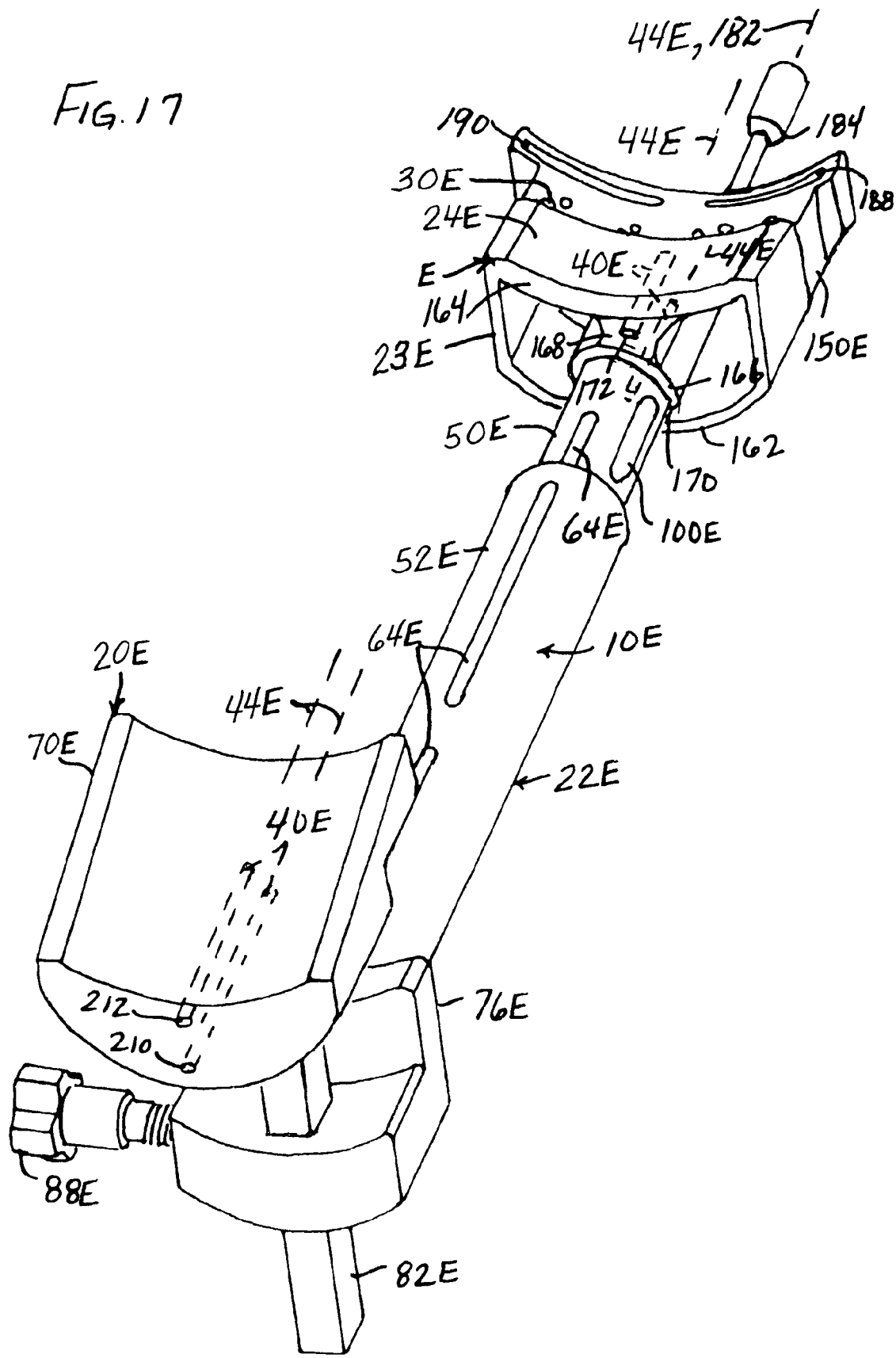
FIG. 17 is a perspective view of the embodiment of FIGS. 15–16.

In the embodiment of FIGS. 15–18 and 19, the body 23E comprises a hollowed-out material to increase its radiolucency. As shown in FIGS. 17 and 30–31, the body 23E includes an anterior wall 162, a posterior wall 164, and a hollow cylindrical member 166 between the anterior and posterior walls 162, 164. The walls of the hollow cylindrical member 166 are connected to the anterior and posterior walls 162, 164 through solid bridges 168, 170. The body includes a pair of bores 172, 174 that are aligned in a sagittal plane. Each bore 172, 174 receives a radiopaque wire, shown at 40 in FIGS. 13–17, that provides a fluoroscopically visible reference for the surgeon; the surgeon can ensure that the alignment guide is properly positioned with respect to the underlying bony landmark: if the surgeon sees more than a single radiopaque line when viewing the guide from the anterior side, then the alignment guide may be improperly positioned, and the surgeon can adjust its position until a single radiopaque line is visible at the first portion when viewed from an anterior perspective. The wires 40D, 40E in the embodiments of FIGS. 13–18 provide co-planar radiopaque longitudinal references 44E.

In the embodiments of FIGS. 13–18, the top member 150D, 150E is mechanically attached to the body 23D, 23E through any suitable means, such as through posts 176D, 176E received in mating holes 178D, 178E (see FIGS. 24 and 31). For durability, the top member in this embodiment may be made of stainless steel or other durable material, and the holes and bores 30D, 30E may be machined into the durable material.

Figure 35:
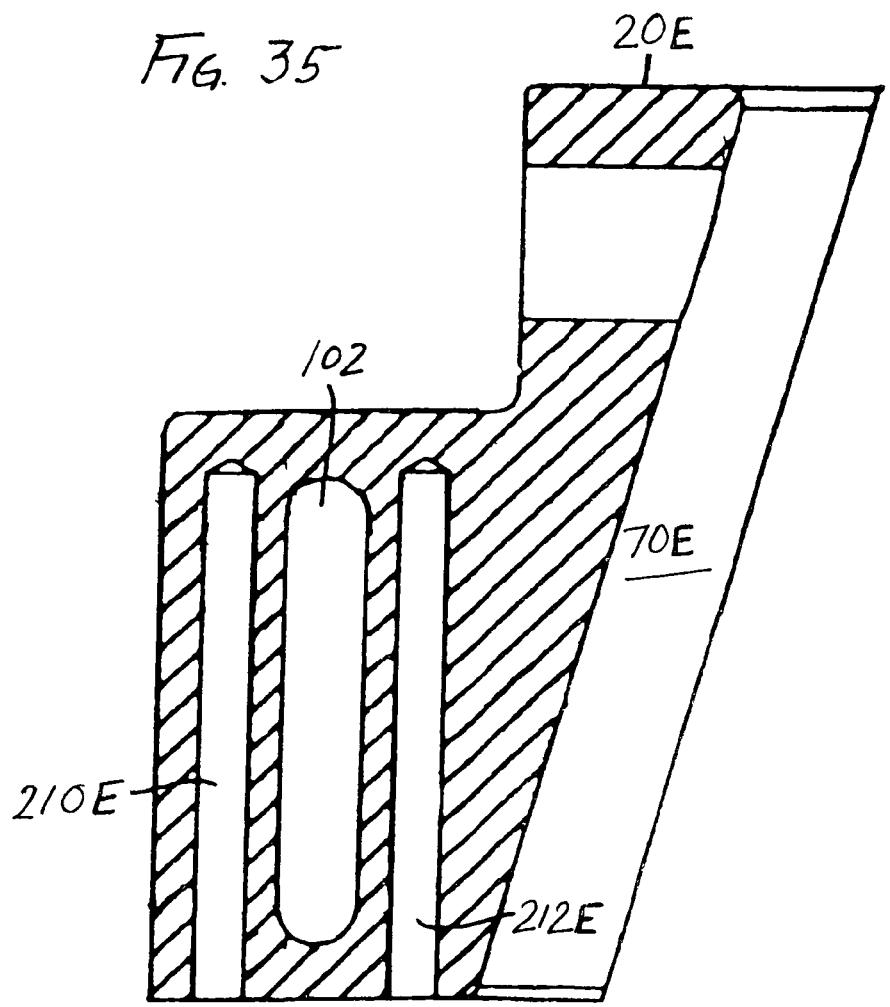
FIG. 35 is a cross-section of the second or distal portion shown in FIG. 34, taken along line 35—35 of FIG. 34.

As shown in FIG. 21, the top surface 36E of the top member 150E may also include a bore 180 having a central longitudinal axis 182 that is aligned to be parallel with the axes of the radiopaque wires 40E. The surgical kit can include a radiopaque reference extender 184. As shown in FIG. 35, the radiopaque reference extender 184 includes a cylindrical base 186 that can be placed in the bore 180 in the top surface 36 of the top member 150, as shown in FIGS. 15–17. The radiopaque reference extender 184 is generally made of a radiopaque material such as stainless steel. With the radiopaque reference extender 184 in place, the longitudinal radiopaque reference provided by the alignment guide is extended proximally past the tibial plateau and joint line to allow the surgeon to reference the position of the alignment guide to additional radiopaque landmarks.

Figure 18:
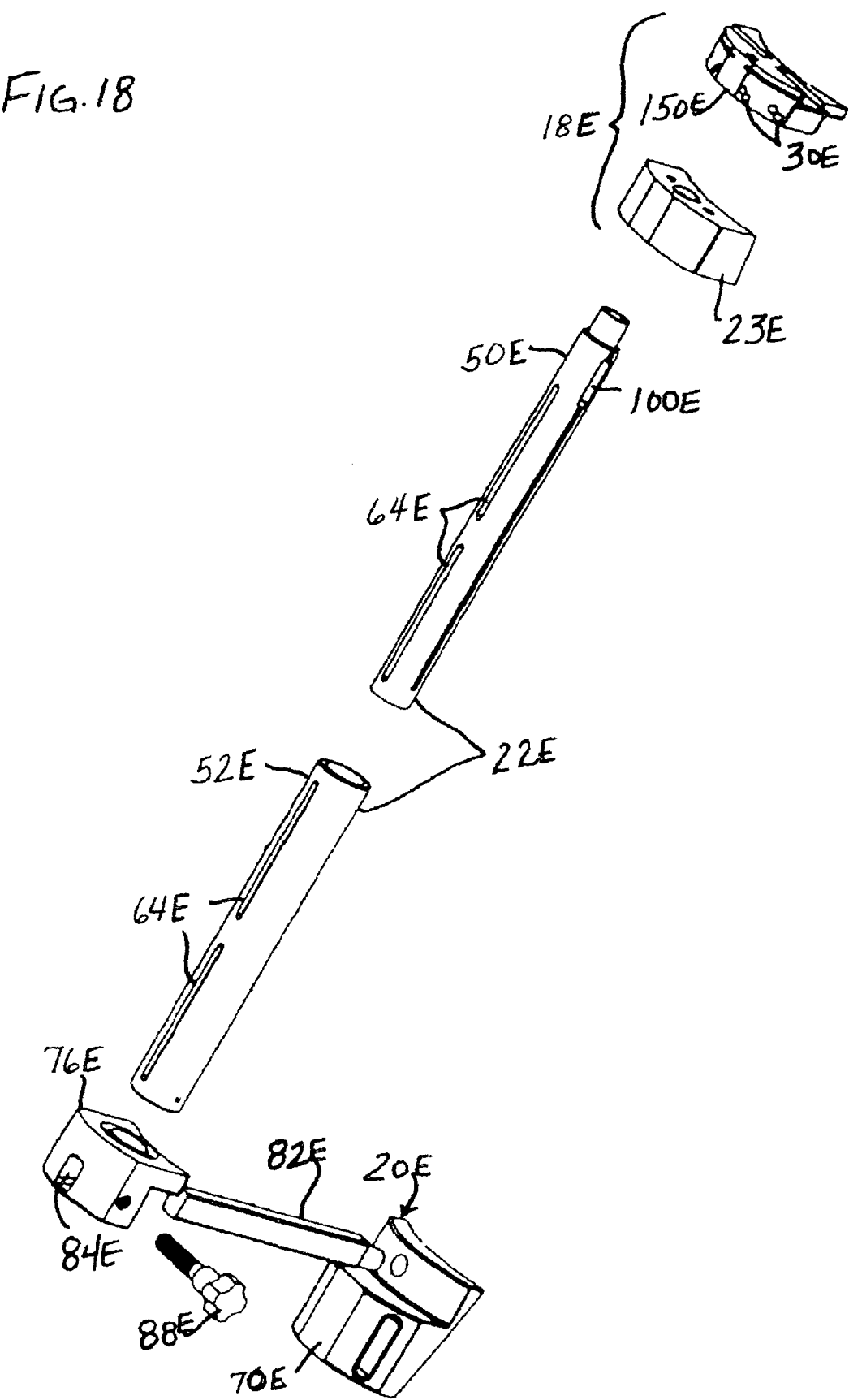
FIG. 18 is an exploded view of the embodiment of FIGS. 15–17, without the radiopaque reference extender and without the fluoroscopy guide pin holder.
Figure 27:
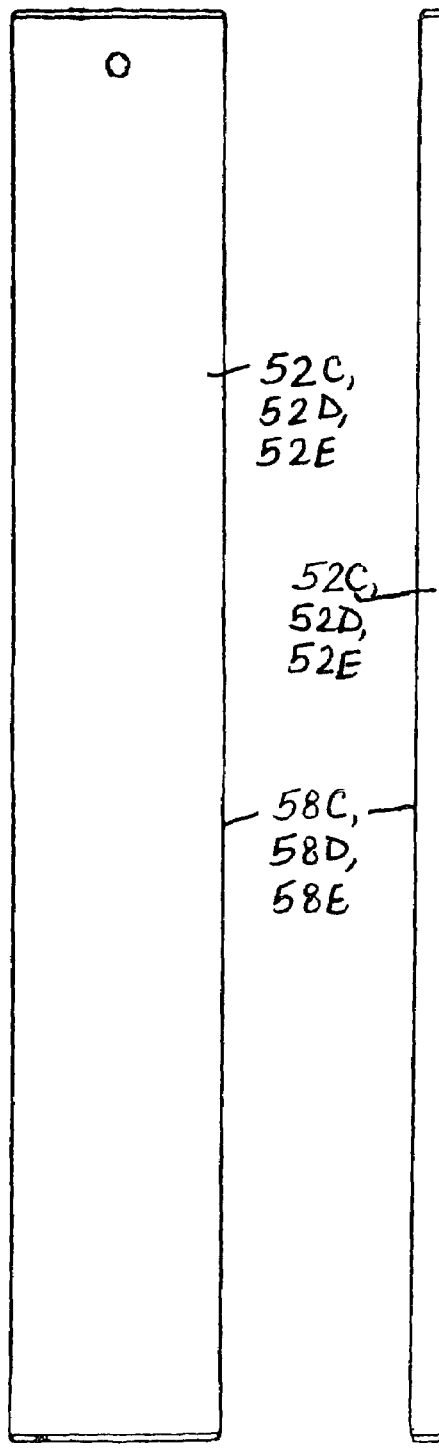
FIG. 27 is an elevation of the other telescoping part of the connecting portion of the guide of FIGS. 4–8 and 13–18.
Figure 28:
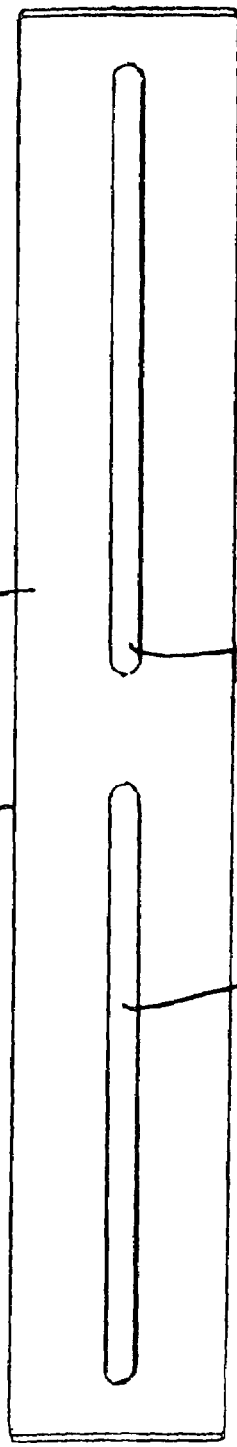
FIG. 28 is an elevation of the part of FIG. 27, rotated 90°.
Figure 29:
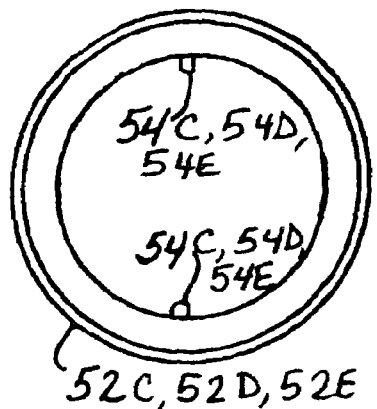
FIG. 29 is an end view of the part of FIGS. 27–28.
Figure 36:
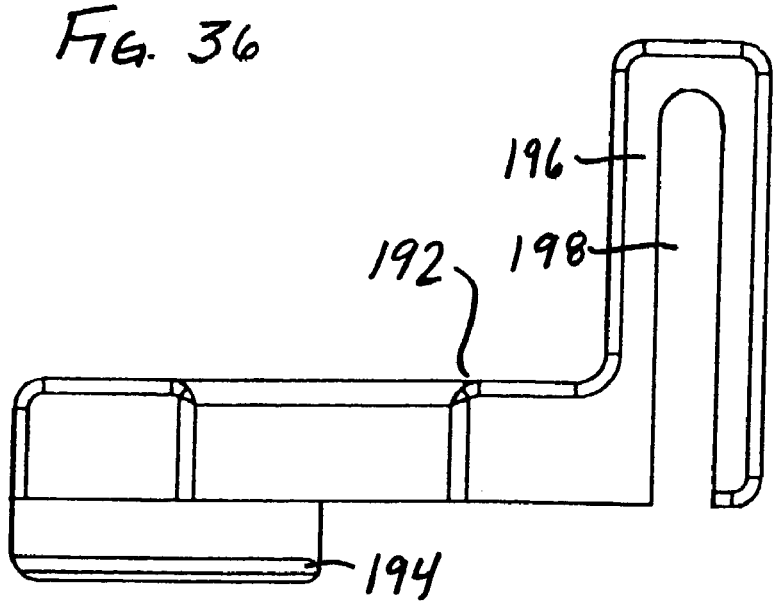
FIG. 36 is an elevation of a fluoroscopy guide pin holder that can be removably mounted on the proximal portion shown in FIGS. 19–20, to create the assembly shown in FIGS. 15–16.
Figure 38:
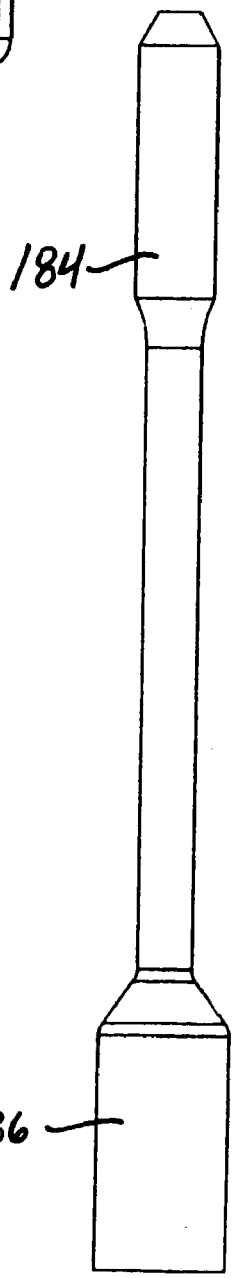
FIG. 38 is an elevation of a radiopaque reference extender.

As shown in FIG. 22, the top member 150E of the embodiment of FIGS. 15–18 also includes a pair of slits 188, 190 extending from the anterior to the posterior sides. The slits 188, 190 are useful not only in providing a mounting area for a stylus as shown in FIG. 11, but also as a means for mounting a separate fluoroscopy guide pin holder 192, illustrated in FIGS. 15–16 and 36. As shown in FIG. 36, the guide pin holder 192 comprises an integral shelf 194 and pin guide 196. The shelf 194 is sized and shaped to be receivable within the slits 188, 190 in the top member 150E so that the guide pin holder 192 can be removably mounted to the top member 150. The pin guide 196 is offset from the shelf 194, and when mounted on the top member 150E, the pin guide 196 extends proximally from the top surface 36E of the top member 150E defining an elongate opening 198 to receive anchoring members such as pins or drills. The first or proximal portion 18E of the alignment guide 10E of FIGS. 15–18 can be used with the guide pin holder 192 alone, as shown in FIGS. 15–17, without the guide pin holder, as shown in FIG. 18, or could be used in simultaneously with or after use of the slope guide 156. If the surgeon so chooses, the guide pin holder 192 can be used to fix the alignment guide against internal/external rotation, while leaving flexibility to adjust the position of the alignment guide 10E in other directions. For example, since the shelf 194 has a smaller dimension in the medial lateral direction than the medial-lateral dimension of the slits 188, 190, the alignment guide 10E can be shifted medially and laterally even after pins have been set through the guide pin holder 192. In addition, even with pins extending through the guide pin holder 192 to the underlying bone, the distal end of the alignment guide 10E can be pivoted upward and downward to set the slope of the alignment guide. Moreover, the overall length of the alignment guide 10E can be adjusted after the pins are in place by the use of a telescoping two-piece connecting portion 22.

It should be understood that the particular mating structures shown for mounting the slope guide 156 and guide pin holder 192 to the top member 150E are provided by way of example only, and may be interchangeable. For example, the guide pin holder 192 could include a base with an undercut to be received in the slots 153, 155, the slope guide 156 could include a shelf to be received in one of the slits 188, 190, or both tools 156, 192 could have similar mounting structures. Other structures that allow these tools 156, 192 to be mounted to some part of the alignment guide 10E could be used.

In the embodiments of FIGS. 13–18, the alignment guide 10D, 10E and tools 156, 184, 192 may be provided as a kit to the surgeon. However, the invention should not be considered to be limited to removable tools 156, 184, 192 as in the illustrated embodiments unless expressly called for in the claims, and should not be considered to be limited to the provision of any particular tool or its functionality unless expressly called for in the claims.

As discussed above, in the embodiments of FIGS. 13–18, the connecting portion 22D, 22E of the alignment guide 10D, 10E comprises two telescoping pieces 50D, 50E, 52D, 52E. Many of the features of the connecting portion 22D, 22E are similar to those of the preceding embodiments. However, in the embodiments of FIGS. 13–18, there is no radiopaque material carried by or in the connecting portion 22D, 22E. Instead, the radiopaque longitudinal reference is provided by the radiopaque wires 40D, 40E carried by the first and, second portions 18D, 18E, 20D, 20E and optionally by the anatomic reference extender 184 in the alignment guide 10E.

In the embodiments of FIGS. 13–18, the first inner part 50D, 50E of the telescoping connecting portion 22D, 22E has a reduced diameter portion 202D, 202E (see FIGS. 25–26) to be received in the hollow cylindrical member 166D, 166E of the top portion 150D, 150E to mount the two portions 50D–50E, 150D, 150E together. The outer part 52D, 52E of the connecting portion 22D, 22E is mounted in a circular groove 204D–204E (see FIG. 32) in the distal end portion 76D, 76E of the connecting portion 22D, 22E. It should be understood that the relative sizes of the telescoping hollow tubes 50D, 50E 52D, 52E of the connecting portion could be reversed in any of the embodiments of FIGS. 4–8 and 13–18, with the outer tube being at the proximal end and the inner tube at the distal end if desired.

The distal end piece 76D, 76E of the connecting portion 22D, 22E of the embodiments of FIGS. 13–18 is illustrated in FIGS. 32–33. As described above, the distal end piece 76D, 76E has a through opening 84D, 84E to receive the rod 82D, 82E of the second distal portion 20D, 20E of the alignment guide. It also has a threaded bore 206D, 206E which receives a threaded screw 88 to lock the relative positions of the distal end piece 76D, 76E and the second distal portion 20D, 20E of the alignment guide.

Figure 34:
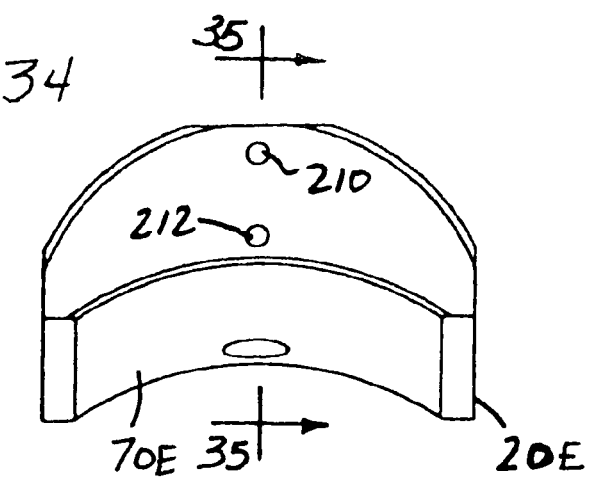
FIG. 34 is a bottom plan view of the second or distal portion of the guide of FIGS. 15–18.

The second or distal portion 20D, 20E of the alignment device of the embodiments of FIGS. 13–18 is illustrated in FIGS. 34–35. As there shown, the posterior surface 70D, 70E of the second or distal portion 20D, 20E is contoured concavely to be stable against the patient's ankle or ankle wrapping. In addition, the posterior surface 70D, 70E of the second portion 20D, 20E of these embodiments 10D, 10E is sloped in a direction opposite to the slope of the posterior surface 24D, 24E of the first portion 18D, 18E of the alignment guide 10D, 10E: the posterior surface 70D, 70E of the second portion 20D, 20E slopes downwardly in a distal direction and the posterior surface 24D, 24E of the first portion 18D, 18E slopes downwardly in a proximal direction.

In the embodiments of FIGS. 13–18, the second or distal portion 20D, 20E of the alignment device carries longitudinal radiopaque references. In both of these embodiments, the second or distal portion 20D, 20E has a pair of parallel bores 210D, 210E, 212D, 212E extending into the radiolucent body of the distal portion 20D, 20E; two radiopaque wires 40D, 40E are carried in these parallel bores 210D, 210E, 212D, 212E as shown in FIGS. 13–17. Each of these radiopaque wires 40D, 40E in the second or distal portion 20D, 20E is aligned to be coplanar with the radiopaque wires 40D, 40E of the first or proximal portion 18D, 18E and with the axis 182 of the hole 180 in the top member 150E of the fifth embodiment 10E. As with the radiopaque wires 40D, 40E in the first portion 18D, 18E, the surgeon can ensure that the alignment guide 10D, 10E is properly positioned with respect to the underlying bony landmark at the ankle: if the surgeon sees more than a single radiopaque line when viewing the guide from the anterior side, then the alignment guide 10D, 10E may be improperly positioned, and the surgeon can adjust its position until a single radiopaque line is visible at the second portion 20D, 20E from an anterior perspective.

As in the case of the first three embodiments, the parts of the alignment guide 10D, 10E of the fourth and fifth embodiments that are not radiopaque can be made of a radiolucent material.

For all of the embodiments, the radiolucent material is preferably one that can be subjected to standard hospital sterilization procedures without substantial degradation. Polymers, copolymers and composites may be used. A heat resistant thermoplastic such as RADEL® polyarylethersulfone (PAES) may be used since it is understood to be sterilizable in a steam autoclave. RADEL® PAES is understood to be available from Amoco Polymers, Inc. of Alpharetta, Ga., and from suppliers such as Piedmont Plastics, Inc. of Charlotte, N.C. It may be desirable to use a different material that is more radiolucent. At least some commercially available acetal copolymers can be used, such as DELRIN® material available from E.I. DuPont de Nemours and Co. of Wilmington, Del. and CELCON® polyoxymethylene available from Celanese Corporation through Ticona-US of Summit, N.J. In addition, aluminum can be used for some of the radiolucent materials. For example, the hollow tubes 50C–50E, 52C–52E of the telescoping connecting portions 22C–22E of the embodiments of FIGS. 4–8 and 13–18 can be made of anodized aluminum. The body 23D, 23E of the first portions 18D, 18E of the embodiments of FIGS. 13–18 can also be made of anodized aluminum. All of the portions or parts could be made of aluminum, and all the parts, whether made of aluminum of polymer or composite, could be hollowed out to improve radioluscense. With these parts being hollow or cast or machined to be substantially hollow, they should be adequately radiolucent. It should be understood that the present invention is not limited to any particular radiolucent material or to any particular degree of radiolucency unless expressly called for in the claims. Generally, use of the term "radiolucent" is intended herein to include any material that will allow the surgeon to view anatomic landmarks either fluoroscopically or radiographically while the alignment guide is in place. For example, the radiolucent material may be at least partially visible fluoroscopically or radiographically, as shown in phantom at 18C in FIG. 12.

For the radiopaque material, it should be understood that the invention is not limited to stainless steel wires. Other forms and shapes of radiopaque materials that could be used include films or coatings of radiopaque material applied directly to the proximal and connecting portions of the alignment device. Instead of elongate shapes, a plurality of other shapes can be used in a variety of patterns; for example, a plurality of spaced radiopaque dots can be set in a linear pattern on the connecting portion of the guide, along with a second set of radiopaque dots set in a differently-oriented linear pattern on the cephalad portion of the guide. Generally, the radiopaque material should be shaped and positioned to provide an instrument reference and to allow and fluoroscopic or radiographic viewing of at least part of the bone so that the position of the alignment guide can be adjusted to align the instrument reference provided by the radiopaque material with the anatomic reference of the bone. Although the present invention provides both longitudinal 44A–44E and transverse radiopaque instrument references 47 48C 49, 159 the invention is not limited to devices using all such instrument references unless expressly set forth in the claims. In addition, although in the illustrated embodiment the transverse and longitudinal radiopaque instrument references 44A–44E, 47, 48C, 49, 159 are perpendicular to each other, in some applications it may be desirable to provide instrument references in other angular relationships. For example, if it is desired to account for normal varus angles, the transverse references 48C, 49 could be set at an angle of, for example, 930 to the longitudinal references 44A–44E. Finally, many of the illustrated radiopaque references are illustrated as being disposed in grooves in the anterior surface of the device 10A–10C such as grooves 46C and 60A–60C, or in bores in the body of the device, such as bores 172, 174, 210D, 210E, 212D, 212E it should be understood that the invention is not limited to such a structure or position unless expressly called for in the claims; the radiopaque material could be disposed on the posterior side of the device or could be secured in the desired position though some other means.

It should also be understood that reference to the elements of the illustrated embodiments as "portions", as in the first, proximal or cephalad portion 18A–18E, the second or distal portion 20A–20E and the connecting portion 22A–22E, does not imply that these elements have any particular shape or structure unless expressly called for in the claims. As illustrated and described above, a suitable extramedullary fluoroscopic alignment guide may be made as a single integral piece, as in the alignment guides 10A, 10B illustrated in FIGS. 1–3A and 3B, or can be made of separate pieces that are assembled into the alignment guide, as in the alignment guide illustrated in FIGS. 4–8 and 13–18. In addition, the portions 18A–18E, 20A–20E, 22A–22E of the alignment guide may have different shapes than those illustrated; for example, the first and connection portions could comprise an integral member with a continuous shape, such as one having an outer surface that is essentially semi-cylindrical. An example of such an alignment guide is illustrated in FIG. 3B at 10B. Other shapes are within the scope of the invention. Thus, "portion" is intended to include both integral and separate elements having the same or different shapes. In addition, the anterior and posterior surfaces of each portion 18A–18E, 20A–20E, 22A–22E may have different contours.

While all the illustrated embodiments are expected to provide many advantages, the alignment guides 10C–10E illustrated in FIGS. 4–8 and 13–18 have an additional advantage: the distance between the proximal portion 18C–18E and distal portion 20C–20E can be adjusted so that the same device can be used on patients with varying tibial lengths. As best seen in comparing FIGS. 6 and 8, this advantage is the result of the telescoping parts 50C, 52C of the connecting portion 22C in this alignment guide 10C. It should be understood that other structures can be used to provide such an advantage. For example, the proximal portion of the alignment guide could be slidable along the connecting portion to allow for adjustment of the distance between the proximal and distal ends.

Additional variations to the illustrated embodiments are contemplated. For example, the proximal or cephalad portion 18 can be designed to accept a cutting block mounted directly to the alignment guide, or the alignment and cutting guides can be made as modular components that reference off of one of the other elements of the device; for example, both a proximal alignment module and cutting block module could be made to reference off of the connecting portion, which can be set and kept in place. The illustrated alignment guides can be used with a complementary cutting block that includes a stem with holes that may slip over the anchoring members 32 to thereby set the cutting block in the proper position after the alignment guide has been slipped off of the anchoring members. Or, the alignment guide could be used with standard cutting blocks that slip onto the anchoring members that are set using the alignment guide. If a separate cutting block is used, the openings 30 provided in the proximal or cephalad portion 18 of the alignment guide may be in the same pattern as the holes in the cutting block so that the cutting block can easily be placed on the anchoring pins or bits. As another alternative, the top member 150 and body 23 could be designed to be detachable so that once the top member 150 is pinned in position, the body 23 and remainder of the alignment guide could be removed while leaving the top member 150 in position to serve as a cutting guide.

It may be desirable to design the cutting block so that when the cutting guide is in place on the anchoring members, the transverse cutting surface for the proximal end of the tibia is at a known, pre-determined distance from the Steinmann pins, so that by positioning the Steinmann pins with the alignment guide, the surgeon simultaneously sets the depth of the cut to be made at the proximal tibia.

The fluoroscopic alignment guide of the present invention may also include structures that hold the guide in a temporary position while the radiographic images are being taken. In the alignment guides 10C–10E of FIGS. 4–8 and 13–18, both the proximal end of the connecting portion 22C–22E and the distal portion 20C–20E include slots 100C–100E 102C–102E formed in the radiolucent material. These slots 100C–100E, 102C–102E may receive elongate webs or straps (not shown) that also extend through commercially available locking mechanisms. These straps may be tightened to hold the alignment guide 10C–10E in a temporary position until the final position is set. The locking mechanism could be a mechanical one or one such as a hook and loop fastener material, for example, commercially-available VELCRO. In the first illustrated embodiment, a pair of removable modular handles, shown at 104 in FIG. 3A, may be provided to cradle the anterior surface of the leg and thereby stabilize the alignment guide 10 on the patient. The modular handles 104 can be made to snap fit or otherwise be fit into mating holes 105 in the body of the connecting portion 22A; preferably, if such handles are to be used, they will be attached to the alignment guide in a manner that allows them to be easily and quickly removed during surgery. It should be understood that other devices could be used to stabilize the alignment guide on the patient during fluoroscopy: for example, spaced spring loaded clamps may be provided.

As discussed above, the fluoroscopic alignment guide 10A–10E may be provided as part of a surgical kit. For the first illustrated embodiment, the kit may include a stylus 28 as shown in FIG. 11 and a special cutting guide with a stem as shown at 106 in FIG. 10. For the embodiment 10C of FIGS. 4–8, the surgical kit may include a stylus 28 and a standard cutting guide.

It should be understood that although the alignment device is referred to herein as a "fluoroscopic" alignment device, the use of the term "fluoroscopic" is not intended to limit use of the device to use in conjunction with fluoroscopic screens. The fluoroscopic alignment guide of the present invention may also be used with radiographic films, and such use should be understood to be included within the expression "fluoroscopic alignment guide".

To make the illustrated fluoroscopic alignment guides 10A–10E the radiolucent polymer can be formed roughly into the illustrated shapes of the proximal, connecting and distal portions 18A–18E, 20A–20E, 22A–22E. The roughly formed portions can be machined into the final illustrated shapes, and the grooves 38A, 38C, 42A–42C 46C, 60A–60C, openings 30A–30E, 64A–64E, 84C–84E, 180, bores, 172, 174, 210D, 210E, 212D, 212E, slits 188, 190 and slots 26, 56C–56E, 100C–100E, 102C–102E, 152, 153, 155 can be machined into the appropriate portions. The radiopaque reference materials can be set into the appropriate grooves 42A–42C, 46C and bores 172, 174, 210D, 210E, 212D, 212E. If grooves are used, the grooves may be formed to allow for a snap fit of the radiopaque reference wires to hold them in place.

Examples of dimensions for the various elements of the illustrated embodiments are as follows. For the first embodiment 10, the overall length from the top surface 36 of the proximal portion 18 to the bottom surface of the distal portion is about 14 inches. The connecting portion has a thickness or width of about 1 inch. The proximal portion is about three inches by two inches, and the distal portion is about 2 inches by about ¾ inch. The longitudinal grooves 42 extend the entire length of the connecting portion and about 1½ inches into the proximal portion 18. The radiopaque material 40 defining the longitudinal radiopaque references 44 need not extend the entire length of the grooves 42, but may be shorter and slid as desired in the grooves or may be made substantially the same lengths as the grooves. Alternatively, a plurality of spaced, shorter longitudinal radiopaque instrument references could be provided at the proximal and distal ends of the guide, although the longitudinal radiopaque instrument references should be of a number, size, shape and should be positioned for medial-lateral alignment to the joint centers, that is, along the mechanical axis of the tibia. FIG. 3B illustrates a fluoroscopic alignment device 13 that has two longitudinally spaced radiopaque wires in each groove 60.

The through openings 64 in the connecting portion 22 are provided in the proximal 8 inches of the connecting portion, and are 0.128 inches wide. For the embodiments 10C–10E of FIGS. 4–8 and 13–18, the bodies of the two end portions 18, 20 are each about three inches by two inches. The entire alignment guide has an overall length in the fully retracted position as shown in FIGS. 4–7 of about 13 inches. The sleeve 52 of the connecting portion 22 has an overall length of about 7 inches. The dimensions of the through openings 64 in the connecting portion may be like those for the first embodiment 10. For the embodiment of FIGS. 4–8, the transverse groove 26 may be dimensioned like those used in standard cutting guides. It should be understood that these dimensions are provided for purposes of illustration only. The present invention is not limited to any particular dimension for any element unless expressly set forth in the claims.

Methods of using the illustrated fluoroscopic alignment guides 10A–10E in surgery are described below. The methods are described with reference to a unicompartmental knee arthroplasty in a minimally invasive procedure. The extramedullary fluoroscopic alignment guides 10A–10E of the present invention are expected to be particularly useful in such minimally invasive surgeries, where there is no opportunity to use an intramedullary alignment system and where the surgeon does not have visual access to many anatomic landmarks except through fluoroscopy or radiography. In some minimally invasive procedures, proper alignment of the tibial resection is particularly important, since resection of the femur is referenced from the resected tibia. However, it should be understood that the present invention is not limited to such procedures: it can be used in more invasive procedures and in total knee arthroplasty. In addition, the method can be used in arthroplasties involving other joints.

The patient is placed supine on the operating table and given a satisfactory anesthetic. A pneumatic tourniquet is placed high on the thigh, and the thigh is placed in a leg holder. The leg is prepped and draped in the usual fashion. FIG. 9 illustrates a portion of a patient's leg 110, with draping 112, and a bandage wrapping 114 around the patient's ankle and foot. The curve of the posterior surface 72 of the distal portion 20 fits against the bandaged ankle as shown in FIG. 9. The foot portion of the operating table is lowered and fluoroscopic equipment is brought in the room and draped with a sterile cover. The patient's leg 110 is elevated, exanquinated and the tourniquet is inflated.

A curved 2–3 inch incision is made at the medial side of the tibial tubercle and extended proximally around the patella. A standard medial retinacular incision is made exposing the medial femoral and tibial condyles. Osteophytes are removed and the anterior-posterior axis of the medial tibial condyle is identified corresponding to the lateral border of the medial femoral condyle. Soft tissue exposure along the proximal medial tibia is performed.

The fluoroscopic alignment guide 10A–10E is brought into the field and the image intensifier is positioned. The leg 110 is extended, and the alignment guide is placed on the anterior surface of the leg above the tibia 14. FIG. 9 illustrates use of the first illustrated extramedullary fluoroscopic alignment guide 10A in position. If the fluoroscopic alignment guide includes temporary stabilizing elements, such as the straps illustrated in the second embodiment, these are tightened to temporarily hold the alignment guide in position. The surgeon and operating room staff may retreat to a safe location and fluoroscopic imaging may then commence. These same steps can be followed with the other embodiments 10B–10E.

With all the illustrated alignment devices 10A–10E, the surgeon may view the fluoroscopic image and compare the positions of the longitudinal radiopaque instrument references 44 to the anatomic references. The surgeon may then adjust the position of the alignment guide 10 until the surgeon is satisfied with the relative positions of the anatomic and radiopaque instrument references 44. The fluoroscopic images may be taken from the anterior perspective as well as from the medial or lateral perspective for use with the first illustrated embodiment. The adjustments to the position of the alignment guide 10 based on the longitudinal radiopaque instrument references 44 will generally comprise adjustments in the medial and lateral directions. The transverse radiopaque instrument reference, if provided, may also be used for adjustments in the proximal-distal direction as well.

If a sufficient part of the tibia is exposed, the surgeon can assess rotation and the level of resection prior to placing the alignment guide 10A–10E on the patient's tibia. The surgeon can visually determine the desired level of tibial resection and set a drill bit or other anchoring member into the patient's bone at this level and in line with the lateral border of the medial femoral condyle. Once this first bit or pin is placed, the surgeon can use it as a physical reference for depth of cut and as a visual reference for internal/external rotation.

To establish proper rotation, the surgeon may alternatively create a vertical groove along the medial compartment of the tibia using the lateral border of the medial femoral condyle as a guide. A device such as a reciprocating saw may be used to create such a vertical groove. The vertical groove may be created with the patient's knee placed in a nearly extended position. Once the vertical groove is established, the drill bit or other device may be set in the vertical groove and the grooves 38 on the transverse top surface 36 of the alignment guide may then be aligned with this drill bit.

Alternatively, rotation can be assessed by aligning the anterior-posterior groove 38 on the top transverse surface 36 of the body 23 of the first or cephalad portion 18 of the alignment guide with the lateral border of the medial femoral condyle. This alignment can be accomplished through visual or fluoroscopic examination of the tibia.

With the embodiment 10E of FIGS. 15–17, the surgeon has another option available when setting internal/external rotation. Proper internal/external tibial rotation can be set through use of the fluoroscopy guide pin holder 192 mounted on the top part 150 of the first portion 18 of the alignment guide. The surgeon can set drills or pins through the elongate opening 198 of the guide pin holder 192. Once pins or drills are so set, further internal/external rotation is limited.

Once proper internal/external rotation is obtained, the surgeon can focus on achieving proper alignment of the alignment guide.

With the alignment guides 10A–10B of FIGS. 1–3B, the surgeon may view the fluoroscopic image and compare the positions of the longitudinal radiopaque instrument reference(s) with bony landmarks and then adjust the position of the guide accordingly. With the alignment guides 10C–10E of FIGS. 4–8 and 13–18, the surgeon may view the fluoroscopic image and compare the positions of the longitudinal and transverse radiopaque instrument references 44, 48 provided by the radiopaque material 40 to the anatomic references. Using such images, the surgeon may then adjust the position of the alignment guide 12 until the surgeon is satisfied with the relative positions of the anatomic and instrument references 44, 48. The fluoroscopic images may preferably be taken from the anterior perspective and from either a medial or lateral perspective.

With all of the illustrated alignment guides, the adjustments to the position of the alignment guide may include medial-lateral adjustments, and adjustments of the entire device in the superior-inferior directions. With the alignments guides of FIGS. 4–8 and 13–18, the surgeon may also make adjustments to the position of the first or cephalad portion 18 in the superior-inferior directions, make adjustments to the overall length of the guide, and make adjustments of orientation in the sagittal plane (slope).

With the embodiments of FIGS. 4–8 and 13–18, the alignment or orientation of the guide 10C–10E may be adjusted in the sagittal plane by sliding the rod 82 of the second or distal portion 20 into or out of the opening 84 at the distal end piece 76 of the connecting portion 22 until the surgeon is satisfied that the slope of the longitudinal instrument reference 44 is at a satisfactory angular relationship to the mechanical or anatomic axis 16 of the tibia 14.

With the alignment guides 10C–10E of FIGS. 4–8 and 13–18, the surgeon may also optimize the position of the first or cephalad portion 18 in the superior-inferior directions. With these alignment guides, the surgeon may insert the foot of a stylus 28 into the transverse slot 26 of the first cephalad portion 18 of the alignment guide 10C of the embodiment of FIGS. 4–8 or into the slits 188, 190 of the embodiment 10E of FIGS. 15–17. The stylus 28 may be used in a standard manner to set the depth of the tibial resection. The end of the stylus outrigger may be extended over the center of the tibial condyle to be resected, and the telescoping parts 50, 52 of the connecting section 22 adjusted until the end of the stylus outrigger rests on the center of the tibial condyle to be resected. Then, the surgeon may desire to verify the position fluoroscopically, by visualizing the positions of the transverse radiopaque instrument reference 159 with respect to anatomic references. Once the surgeon is satisfied with the position of the first or cephalad portion 18 of the alignment device 12, additional anchoring members can then be set through the circular openings 30 in the first or cephalad portion 18 of the alignment guide 10C–10E. The number of anchoring members set in the proximal tibia can be less than the number used in standard procedures to set a tibial cutting guide, block or jig because of the additional stability provided by the pins that define the mechanical axis.

With a slope guide 156 as in the embodiment 10D of FIGS. 13–14, the surgeon can set the slope of the alignment device 10D in a sagittal plane at an angular relationship based on the tibial plateau. The transverse radiopaque reference 159 provided by the slope guide 156 can be aligned with the patient's tibial posterior slope, and the longitudinal radiopaque references 44 will be perpendicular to the transverse reference 159. The surgeon can adjust the relative positions of the second or distal portion 20 and connecting portion 22 until the alignment guide is at the proper slope and supported by the distal portion 20 resting on the ankle.

Figure 10:
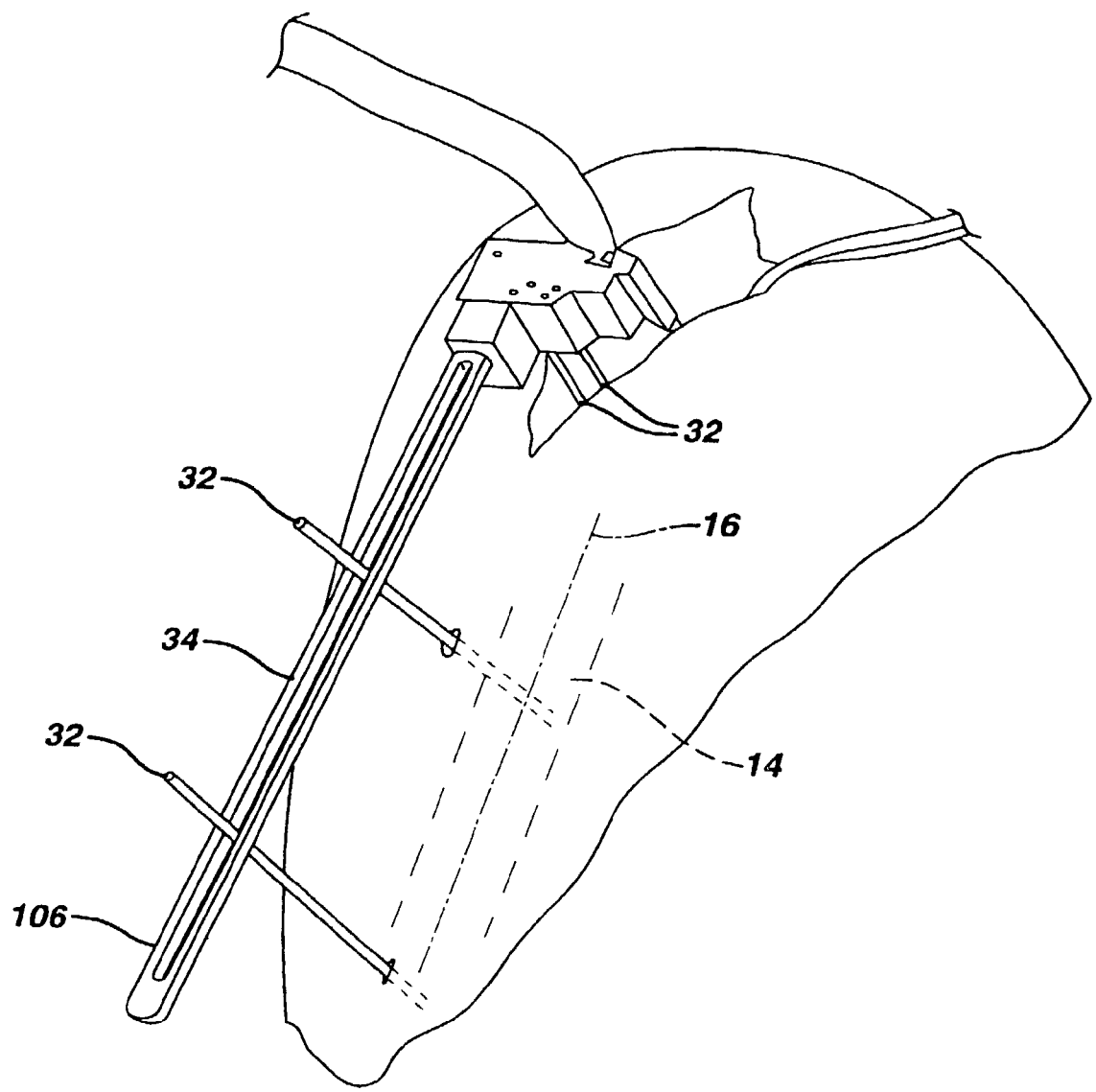
FIG. 10 is a perspective illustration of a cutting guide mounted on the Steinmann pins set as shown in FIG. 9, on the anterior surface of the leg, after the alignment guide has been removed.

With the alignment guide stabilized on the patient's leg, the illustrated embodiments offer the surgeon different options. With all of the illustrated embodiments, the surgeon can remove the alignment guide 10, leaving the anchoring members 32 in place. A cutting guide or jig 106 may then be used like that shown in FIG. 10, for example. This cutting guide 106 includes an elongate stem 118 that has an elongate slot 120. The elongate slot 120 on the stem 118 is designed to register with the anchoring members 32 that were set through the openings 64 in the connecting member 22 of the alignment guide 10. The elongate slot 120 of the stem 118 of the cutting guide 106 is then aligned with the previously-set anchoring members 32 and the cutting guide 106 is then placed on the previously-set anchoring members 106 as shown in FIG. 10. Thus, the cutting guide 106 can be set along the mechanical axis 16 of the bone 14. The cutting guide or jig 106 could be adjusted in the superior-inferior direction to set the desired depth of tibial resection. A standard stylus 28 may be used for this purpose. Posterior angulation may similarly be adjusted and the cutting guide or jig 106 may then be secured to the proximal tibia using anchoring members such as pins or drill bits. Bone cuts can then be made accordingly using the cutting guide 106.

The embodiments 10D, 10E of FIGS. 13–18 offer an additional option to the surgeon: the surgeon may use the slits 188, 190 or the top surface 36D, 36E of the top portion 150D, 150E as a guide surface and cut the proximal tibia directly off of the alignment guide 10D, 10E, without removing any portion of the alignment guide.

As discussed above, it may also be desirable to provide a modular system that allows the cutting guide or jig to be mounted directly to all or some portion of the alignment guide, or to allow the body 23E of the guide to be removed after the cutting portion 150E has been positioned. This latter option potentially could allow the cutting portion 150E to be advanced into the wound and closer to the bone to facilitate cutting.

It should be understood that the above surgical procedures are provided as examples of use of the illustrated extramedullary fluoroscopic alignment guides 10A–10E. Claims directed to the alignment guide and to surgical kits including the alignment guide are not limited to the surgical procedures described above. Moreover, claims directed to surgical methods should not be construed to be limited to any particular device or structure unless expressly set forth in the claims.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

I claim:

1. An extramedullary fluoroscopic alignment guide to be fixed to a bone with an anchoring member during orthopaedic surgery wherein part of the bone is to be resected, the bone having an anatomic reference and a mechanical axis, the alignment guide comprising:

a first portion shaped to be positioned on a patient's limb at one end of a long bone, the first portion comprising a radiolucent body having radiopaque material shaped and positioned to define a linear longitudinal radiopaque reference;

a second portion shaped to be positioned on a patient's limb at the opposite end of the long bone, the second portion including a radiolucent body having radiopaque material shaped and positioned to define a linear longitudinal radiopaque reference;

an elongate connecting portion extending between the first portion and the second portion, the elongate connecting portion having a longitudinal axis, the longitudinal axis of the elongate portion and the linear longitudinal radiopaque references of the first portion and second portion being parallel to each other;

wherein the elongate connecting portion comprises radiolucent material to allow fluoroscopic viewing of at least part of the bone so that the position of the alignment guide can be adjusted to align the radiopaque instrument reference with at least part of the bone;

wherein the elongate connecting portion includes a transverse through opening sized, shaped and positioned to receive an anchoring pin for fixing the position of the alignment guide with respect to the bone;

and wherein the first portion, second portion and elongate connecting portion have an overall length sufficient to extend over at least a substantial part of the length of the long bone.

2. The fluoroscopic alignment guide of claim 1, wherein the radiopaque material is associated with the connecting portion of the alignment guide.

3. The fluoroscopic alignment guide of claim 1, wherein the radiopaque material is associated with the connecting portion of the alignment guide.

4. The fluoroscopic alignment guide of claim 1, further comprising radiopaque material, shaped and positioned to provide a radiopaque transverse instrument reference.

5. The fluoroscopic alignment guide of claim 1, wherein the radiopaque material is sized, shaped, and positioned to provide a radiopaque transverse instrument reference.

6. The fluoroscopic alignment guide of claim 1, wherein the elongate connecting portion includes a plurality of longitudinally spaced transverse through slots to receive anchoring pins.

7. The fluoroscopic alignment guide of claim 1, wherein the first portion of the alignment guide includes a plurality of openings to receive anchoring members.

8. The fluoroscopic alignment guide of claim 1, wherein the second portion of the alignment guide includes a posterior surface contoured to bear against a portion of the patient's body and the first portion includes a posterior surface contoured to bear against a different portion of the patient's body.

9. The fluoroscopic alignment guide of claim 1, wherein first and second portions have posterior surfaces that are concavely contoured.

10. The fluoroscopic alignment guide of claim 1, wherein the second portion is connected to the connecting portion through a connection that allows relative movement between the second portion and the connecting portion along an axis defining an angle with the longitudinal axis of the connecting portion.

11. The fluoroscopic alignment guide of claim 1, wherein the distance between the first and second portions is adjustable.

12. The fluoroscopic alignment guide of claim 11, wherein the connecting portion comprises two telescoping parts to allow for adjustment of the distance between the first and second portions.

13. The fluoroscopic alignment guide of claim 1, wherein the first portion, second portion and connecting portion comprise an integral piece.

14. The fluoroscopic alignment guide of claim 1, comprising an assembly of separate elements.

* * * * *